(12) United States Patent
Leighton et al.

(10) Patent No.: US 9,380,769 B2
(45) Date of Patent: Jul. 5, 2016

(54) TRANSGENIC CHICKEN COMPRISING AN INACTIVATED IMMUNOGLOBULIN GENE

(75) Inventors: Phil Leighton, San Francisco, CA (US); William Don Harriman, Alameda, CA (US); Robert Etches, Oakland, CA (US)

(73) Assignee: Crystal Bioscience Inc., Emeryville, CA (US)

(*) Notice: Subject to any disclaimer, the term of this patent is extended or adjusted under 35 U.S.C. 154(b) by 0 days.

(21) Appl. No.: 14/114,159

(22) PCT Filed: May 23, 2012

(86) PCT No.: PCT/US2012/039191
§ 371 (c)(1),
(2), (4) Date: Nov. 18, 2013

(87) PCT Pub. No.: WO2012/162422
PCT Pub. Date: Nov. 29, 2012

(65) Prior Publication Data
US 2014/0082759 A1    Mar. 20, 2014

Related U.S. Application Data

(60) Provisional application No. 61/489,638, filed on May 24, 2011.

(51) Int. Cl.
| | | |
|---|---|---|
| A01K 67/027 | (2006.01) | |
| C12N 5/16 | (2006.01) | |
| C12N 15/87 | (2006.01) | |
| C12N 15/90 | (2006.01) | |

(52) U.S. Cl.
CPC .......... *A01K 67/0276* (2013.01); *C12N 15/902* (2013.01); *A01K 2217/075* (2013.01); *A01K 2217/15* (2013.01); *A01K 2227/30* (2013.01)

(58) Field of Classification Search
None
See application file for complete search history.

(56) References Cited

U.S. PATENT DOCUMENTS

| | | |
|---|---|---|
| 6,114,598 A | 9/2000 | Kucherlapati et al. |
| 2002/0028488 A1 | 3/2002 | Singh et al. |
| 2010/0138946 A1 | 6/2010 | Van De Lavoir et al. |

FOREIGN PATENT DOCUMENTS

| | | |
|---|---|---|
| WO | WO03081992 | 10/2003 |
| WO | WO2009023800 | 2/2009 |
| WO | WO2011019844 | 2/2011 |

OTHER PUBLICATIONS

Lillico et al. (hereinafter "Lillico"; Drug Disc. Today 2005; 10(3)191-196.*
Hillier et al., Nature 2004, 432:695-716.*
Database Accession No. M30320, "Gallus gallus Ig germline heavy chain J segment (JH) gene.", 1994, 1 page.
Reynaud, et al., "Somatic hyperconversion diversifies the single VH gene of the chicken with a high incidence in the D region", vol. 59, No. 1,1989, pp. 171-183.
Adachi, et al. "Gene targeting using the human Nalm-6 pre-B cell line", BioScience Trends 2008; 2(5):169-180.
Meek, et al. "Efficient Gene Targeting by Homologous Recombination in Rat Embryonic Stem Cells", PLoS ONE | www.plosone.org, Dec. 2010, vol. 5, Issue 12, e14225, pp. 1-6.
Sakurai, et al. "Efficient integration of transgenes into a defined locus in human embryonic stem cells", Nucleic Acids Research, 2010, vol. 38, No. 7, e96, pp. 1-8.
Tong, et al. "Production of p53 gene knockout rats by homologous recombination in embryonic stem cells", Nature, vol. 467, 2010, pp. 211-215.

\* cited by examiner

*Primary Examiner* — Doug Schultz
(74) *Attorney, Agent, or Firm* — James S. Keddie; Bozicevic, Field & Francis, LLP

(57) ABSTRACT

A transgenic chicken comprising an inactivated heavy immunoglobulin gene and/or inactivated light chain immunoglobulin gene is provided, as well as cells and targeting vectors for making the same.

4 Claims, 9 Drawing Sheets

From published sequence and existing genome databases:

Crystal IgH sequence:

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
actgtgctgc aggtggctat g                                             21

<210> SEQ ID NO 2
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 2
atacgatgtt ccagattacg ctt                                           23

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
actgtgctgc aggtggctat g                                             21

<210> SEQ ID NO 4
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 4
tcagcagcag cagtgcggac                                                  20

<210> SEQ ID NO 5
<211> LENGTH: 18586
<212> TYPE: DNA
<213> ORGANISM: Artificial sequence
<220> FEATURE:
<223> OTHER INFORMATION: Synthetic plasmid construct

<400> SEQUENCE: 5
ctaaattgta agcgttaata ttttgttaaa attcgcgtta aattttttgtt aaatcagctc      60 attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat gggtaccgg     660 cgcgcccatc actcagggag gagatggtcc cagcagcctt gtccctgccc tgcactgcac     720
ttagctcctg gaccccatct cctgctgccc acccatattg cctccctgtg ttgctgttgc     780
agggttgctt ctgcctcata ctggtttctc ccttctggag gtggccaaaa gccgggccct     840
gtgcaatcct ggtgcataaa taccttatgg cccctaagta gggcaggtgt gggacacgct     900
ctggcacctg gggtgtgtgc aagtgctcag gaagacctgc aggcacaggt ggcagtgggg     960
ggtctctggc tgtgctcgag cagcagctgc ctggggtaag ggtagtactc tgtgcatgaa    1020
caatgctgca gggctcagct ctgctcagac cacgaccctg gcaccaacag agacctgcct    1080
ggctctgtgg tcatgtaaac ctttacagga gctcaagaca aggctgttta ttactgctct    1140
ggcaggaaag aagcactggc catggtcata gagagttcca gcaacaggaa agtgagagcc    1200
caagctgctg aggtaccagg gctcctcagg tgcctgctgc agcagcttgg acacagtcga    1260
ggaacagcaa ttgtacctgt gtggtggatc aggctgtgct gcctgtgaac ctattctagc    1320
acatctgtca cctctgtgcc actcacaggg ataccacccc tgagacccct accccatcag    1380
cctctgtgtg ggatatggtg ttgggcccaa gggctctgtt gcacagggag atagaggcct    1440
ggggaggagg gaaagcattg aggtggtgtt gataccaggg atgtgagccc aagcaagaga    1500
tcagcagagc aaggaggaag aattgcaggt gttgggctg gggaaagccc cagatggctg    1560
gagctggtgg ggccactgga gatcctcctcc tccatcctg ctccatgctg ggcagctgc    1620 tgcaggctga ccagggcctg cccgggcacg ttgtgaaggt caccaaggat ggagacttca    1680
gagctagcat aacttcgtat agcatacatt atacgaagtt ataagcgtaa tctggaacat    1740
cgtatgtacc ggatccgaag caggcttttcc tggaaggtcc tggaagggg cgtccgcggg    1800 agctcacggg gacagccccc ccccaaaagcc cccagggatg taattacgtc cctccccgc    1860
```

```
tagggggcag cagcgagccg cccggggctc cgctccggtc cggcgctccc cccgcatccc   1920
cgagccggca gcgtgcgggg acagcccggg cacggggaag gtggcacggg atcgctttcc   1980
tctgaacgct tctcgctgct ctttgagcct gcagacacct gggggggatac ggggaaaaag   2040
ctttaggctg agaagcaggc tttcctggaa ggtcctggaa gggggcgtcc gcgggagctc   2100
acggggacag cccccccca aagccccag ggatgtaatt acgtccctcc cccgctaggg     2160
ggcagcagcg agccgcccgg ggctccgctc cggtccggcg ctcccccgc atccccgagc    2220
cggcagcgtg cggggacagc ccgggcacgg ggaaggtggc acgggatcgc tttcctctga   2280
acgcttctcg ctgctctttg agcctgcaga cacctggggg gatacgggga aaaagcttta   2340
ggctgaacta gctagtctcg aggtcgaggt gagccccacg ttctgcttca ctctccccat   2400
ctcccccccc tccccacccc caattttgta tttatttatt ttttaattat tttgtgcagc   2460
gatggggcg ggggggggg gggcgcgcgc caggcggggc gggcggggc gaggggcggg      2520
gcggggcgag gcggagaggt gcggcggcag ccaatcagag cggcgcgctc cgaaagtttc   2580
cttttatggc gaggcggcgg cggcggcggc cctataaaaa gcgaagcgcg cggcgggcgg   2640
gagtcgctgc gttgccttcg ccccgtgccc cgctccgcgc cgcctcgcgc cgcccgcccc   2700
ggctctgact gaccgcgtta ctcccacagg tgagcgggcg ggacgccct tctcctccgg    2760
gctgtaatta gcgcttggtt taatgacggc tcgtttcttt tctgtggctg cgtgaaagcc   2820
ttaaagggct ccgggagggc cctttgtgcg ggggggagcg gctcgggggg tgcgtgcgtg   2880
tgtgtgtgcg tggggagcgc cgcgtgcggc ccgcgctgcc cggcggctgt gagcgctgcg   2940
ggcgcggcgc ggggctttgt gcgctccgcg tgtgcgcgag gggagcgcgg ccggggggcgg  3000
tgccccgcgg tgcgggggg ctgcgagggg aacaaaggct gcgtgcgggg tgtgtgcgtg    3060
ggggggtgag caggggtgt gggcgcgcg gtcgggctgt aaccccccc tgcacccccc      3120
tccccgagtt gctgagcacg gcccggcttc gggtgcgggg ctccgtgcgg ggcgtggcgc   3180
ggggctcgcc gtgccgggcg gggggtggcg gcaggtgggg gtgccgggcg gggcggggcc   3240
gcctcgggcc ggggagggct cgggggaggg gcgcggcggc cccggagcgc cggcggctgt   3300
cgaggcgcgc cgagccgcag ccattgccctt ttatggtaat cgtgcgagag ggcgcaggga  3360
cttcctttgt cccaaatctg gcggagccga aatctgggag gcgccgccgc acccctcta   3420
gcgggcgcgg gcgaagcggt gcggcgccgg caggaaggaa atgggcgggg agggccttcg   3480
tgcgtcgccg cgccgccgtc cccttctcca tctccagcct cggggctgcc gcagggggac   3540
ggctgccttc gggggggacg gggcagggcg gggttcggct tctggcgtgt gaccggcggc   3600
tctagagcct ctgctaacca tgttcatgcc ttcttctttt tcctacagct cctgggcaac   3660
gtgctggttg ttgtgctgtc tcatcatttt ggcaaagaat tatcgcatgc ctgcgtcgac   3720
ggtaccgcgg gcccgggatc caccggtcgc caccatggtg agcaagggcg aggagctgtt   3780
caccggggtg gtgcccatcc tggtcgagct ggacggcgac gtaaacggcc acaagttcag   3840
cgtgtccggc gagggcgagg gcgatgccac ctacggcaag ctgaccctga agttcatctg   3900
caccaccggc aagctgcccg tgccctggcc caccctcgtg accaccctga cctacggcgt   3960
gcagtgcttc agccgctacc ccgaccacat gaagcagcac gacttcttca agtccgccat   4020
gcccgaaggc tacgtccagg agcgcaccat cttcttcaag gacgacggca actacaagac   4080
ccgcgccgag gtgaagttcg agggcgacac cctggtgaac cgcatcgagc tgaagggcat   4140
cgacttcaag gaggacggca acatcctggg gcacaagctg gagtacaact acaacagcca   4200
caacgtctat atcatggccg acaagcagaa gaacggcatc aaggtgaact tcaagatccg   4260
```

```
ccacaacatc gaggacggca gcgtgcagct cgccgaccac taccagcaga acacccccat    4320
cggcgacggc cccgtgctgc tgcccgacaa ccactacctg agcacccagt ccgccctgag    4380
caaagacccc aacgagaagc gcgatcacat ggtcctgctg gagttcgtga ccgccgccgg    4440
gatcactctc ggcatggacg agctgtacaa gtaaagcggc cggccgcgac tctagatcat    4500
aatcagccat accacatttg tagaggtttt acttgcttta aaaaacctcc cacacctccc    4560
cctgaacctg aaacataaaa tgaatgcaat tgttgttgtt aacttgttta ttgcagctta    4620
taatggttac aaataaagca atagcatcac aaatttcaca ataaagcat tttttttcact    4680 gcattctagt tgtggtttgt ccaaactcat caatgtatct taaggaaccc cttcctcgac    4740
attgattatt gactagctag ttattaatag taatcaatta cggggtcatt agttcatagc    4800
ccatatatgg agttccgcgt tacataactt acggtaaatg gcccgcctgg ctgaccgccc    4860
aacgaccccc gcccattgac gtcaataatg acgtatgttc ccatagtaac gccaataggg    4920
actttccatt gacgtcaatg ggtggactat ttacggtaaa ctgcccactt ggcagtacat    4980
caagtgtatc atatgccaag tacgcccccct attgacgtca atgacggtaa atggcccgcc    5040
tggcattatg cccagtacat gaccttatgg gactttccta cttggcagta catctacgta    5100
ttagtcatcg ctattaccat gggtcgaggt gagccccacg ttctgcttca ctctccccat    5160 ctccccccccc tccccacccc caattttgta tttatttatt ttttaattat tttgtgcagc    5220 gatggggcg gggggggggg gggcgcgcgc caggcggggc ggggcgggc gaggggcggg    5280 gcggggcgag gcggagaggt gcggcggcag ccaatcagag cggcgcgctc cgaaagtttc    5340
cttttatggc gaggcggcgg cggcggcggc cctataaaaa gcgaagcgcg cggcgggcgg    5400
gagtcgctgc gttgccttcg ccccgtgccc cgctccgcgc cgcctcgcgc cgcccgcccc    5460
ggctctgact gaccgcgtta ctcccacagg tgagcgggcg ggacgccct tctcctccgg    5520 gctgtaatta gcgcttggtt taatgacggc tcgtttcttt tctgtggctg cgtgaaagcc    5580
ttaaagggct ccgggagggc cctttgtgcg ggggggagcg gctcggggg tgcgtgcgtg    5640 tgtgtgtgcg tggggagcgc cgcgtgcggc ccgcgctgcc cggcggctgt gagcgctgcg    5700
ggcgcggcgc ggggctttgt gcgctccgcg tgtgcgcgag gggagcgcgg ccggggcgg    5760 tgccccgcgg tgcgggggg ctgcgagggg aacaaaggct gcgtgcgggg tgtgtgcgtg    5820 gggggtgag caggggtgt gggcgcgcg gtcgggctgt aaccccccccc tgcacccccc    5880 tccccgagtt gctgagcacg gcccggcttc gggtgcgggg ctccgtgcgg ggcgtggcgc    5940
ggggctcgcc gtgccgggcg gggggtggcg gcaggtgggg gtgccgggcg gggcggggcc    6000
gcctcgggcc ggggagggct cggggagggg gcgcggcggc cccggagcgc cggcggctgt    6060
cgaggcgcgg cgagccgcag ccattgcctt ttatggtaat cgtgcgagag ggcgcaggga    6120
cttcctttgt cccaaatctg gcggagccga aatctgggag gcgccgccgc accccctcta    6180
gcgggcgcgg gcgaagcggt gcggcgccgg caggaaggaa atgggcgggg agggccttcg    6240
tgcgtcgccg cgccgccgtc cccttctcca tctccagcct cggggctgcc gcaggggac    6300 ggctgccttc ggggggacg gggcagggcg gggttcggct tctggcgtgt gaccggcggc    6360
tctagagcct ctgctaacca tgttcatgcc ttcttctttt tcctacagct cctgggcaac    6420
gtgctggtta ttgtgctgtc tcatcatttt ggcaaagaat tcctagcgcc accatgaccg    6480
agtacaagcc taccgtgcgc ctggccactc gcgatgatgt gcccgcgcc gtccgcactc    6540 tggccgccgc tttcgccgac taccccgcta cccggcacac cgtggacccc gaccggcaca    6600
tcgagcgtgt gacagagttg caggagctgt tcctgacccg cgtcgggctg gacatcggca    6660
```

```
aggtgtgggt agccgacgac ggcgcggccg tggccgtgtg gactaccccc gagagcgttg   6720
aggccggcgc cgtgttcgcc gagatcggcc cccgaatggc cgagctgagc ggcagccgcc   6780
tggccgccca gcagcaaatg gagggcctgc ttgccccccca tcgtcccaag gagcctgcct   6840
ggtttctggc cactgtagga gtgagcccg accaccaggg caagggcttg ggcagcgccg    6900
tcgtgttgcc cggcgtagag gccgccgaac gcgccggtgt gcccgccttt ctcgaaacaa   6960
gcgcaccaag aaaccttcca ttctacgagc gcctgggctt caccgtgacc gccgatgtcg   7020
aggtgcccga gggacctagg acctggtgta tgacacgaaa acctggcgcc taatgatcta   7080
gaaccggtca tggccgcaat aaaatatctt tattttcatt acatctgtgt gttggttttt   7140
tgtgtgttcg aacctgcagc cgggggatc cgaagcaggc tttcctggaa ggtcctggaa   7200
gggggcgtcc gcgggagctc acggggacag ccccccccca aagcccccag ggatgtaatt   7260
acgtccctcc cccgctaggg ggcagcagcg agccgcccgg ggctccgctc cggtccggcg   7320 ctcccccgc atcccgagc cggcagcgtg cggggacagc ccgggcacgg ggaaggtggc    7380
acgggatcgc tttcctctga acgcttctcg ctgctctttg agcctgcaga cacctggggg   7440
gatacgggga aaaagcttta ggctgagaag caggcttcc tggaaggtcc tggaaggggg    7500
cgtccgcggg agctcacggg gacagccccc ccccaaagcc cccagggatg taattacgtc   7560 cctccccgc tagggggcag cagcgagccg cccggggctc cgctccggtc ggcgctccc    7620 cccgcatccc cgagccggca gcgtgcgggg acagcccggg cacggggaag gtggcacggg   7680
atcgctttcc tctgaacgct ctcgctgct ctttgagcct gcagacacct gggggatac    7740 ggggaaaaag cttaggctg aactagaatg catataactt cgtatagcat acattatacg    7800
aagttatgga tcccccaaat caatctaaag tatatatgag taacctgagg ctatggcagg   7860
gcctgccgcc ccgacgttgg ctgcgagccc tgggccttca cccgaacttg ggggtgggg    7920 tggggaaaag gaagaaacgc gggcgtattg gccccaatgg ggtctcggtg gggtatcgac   7980
agagtgccag ccctgggacc gaaccccgcg tttatgaaca aacgaccccaa caccgtgcgt   8040 tttattctgt cttttattg ccgtcatagc gcgggttcct tccggtattg tctccttccg    8100
tgtttcagtt agcctccccc tagggtgggc gaagaactcc agcatgagat ccccgcgctg   8160
gaggatcatc cagccggcgt cccggaaaac gattccgaag cccaaccttt catgaaggc   8220 ggcggtggaa tcgaaatctc gtgatggcag gttgggcgtc gcttggtcgg tcatttcgaa    8280
ccccagagtc ccgctcagaa gaactcgtca agaaggcgat agaaggcgat gcgctgcgaa    8340
tcgggagcgg cgataccgta aagcacgagg aagcggtcag cccattcgcc gccaagctct    8400
tcagcaatat cacgggtagc caacgctatg tcctgatagc ggtccgccac acccagccgg    8460
ccacagtcga tgaatccaga aaagcggcca ttttccacca tgatattcgg caagcaggca    8520
tcgccatggg tcacgacgag atcctcgccg tcgggcatgc tcgccttgag cctggcgaac    8580
agttcggctg cgcgagccc ctgatgctct tcgtccagat catcctgatc gacaagaccg    8640
gcttccatcc gagtacgtgc tcgctcgatg cgatgtttcg cttggtggtc gaatgggcag    8700
gtagccggat caagcgtatg cagccgccgc attgcatcag ccatgatgga tactttctcg    8760
gcaggagcaa ggtgagatga caggagatcc tgccccggca cttcgcccaa tagcagccag    8820 tcccttccg cttcagtgac aacgtcgagc acagctgcgc aaggaacgcc cgtcgtggcc    8880
agccacgata gccgcgctgc ctcgtcttgc agttcattca gggcaccgga caggtcggtc    8940
ttgacaaaaa gaaccgggcg cccctgcgct gacagccgga acacggcggc atcagagcag    9000
ccgattgtct gttgtgccca gtcatagccg aatagcctct ccacccaagc ggccggagaa    9060
```

```
cctgcgtgca atccatcttg ttcaatcatg cgaaacgatc ctcatcctgt ctcttgatcg    9120
attacgcccc caactgagag aactcaaagg ttaccccagt tggggcacac tagtgctgac    9180
tctgcatcca tgtctctgtg tccttttgcg tgctgtctgc atctcacaca gtggggtcag    9240
ccccagtatg gggaagggct gggggggcgca tacacacata ttggtaatgt tggggggcggg   9300 gggggggtgg gggggtcaac agatcagcac tggagacact ggtgtatacc ctggcaccac    9360
caacatctaa ggcagggtgc tttggggcaa ttttggggca gtttaaggtc tgtgctggca    9420
ctgagcacgt ggctgtggcc gtgctgtcct catctcccac ccactacggt ctgtgcgcca    9480
ggtccctagc agagatttgc tttatgctgg aacaggggg agttctgggt ctgtttcctt    9540
gcattcagac ccctggtgc ccctgggtg ggatgtcagt gtgaatactc ctttgtgccc    9600
tgtgcctgca gcagcctgac cctccacaca ccacacgcct tgtgtgcacc ccaccccctgt    9660 cactatccct ctccccgctc cccagggaga ttttgcagtg gccctgtag ggcagctttt    9720 agcacagccc ccagcagcaa gcaagcagaa agcactgctg tgcacagctt gtcagctgtg    9780
tgtgtttgct gaggaggatc tgtctttttgc tgaggccatc agtcttgtcc tgctcaacct    9840
ccatcgatgc tgcccacctc aacacatcta cccatctatt ccatctacac caacatctcc    9900
attcatccca cccacccaaa catgtccatc catcacaaca cctccatcca acccgcacac    9960
tccagcacct ccaatcattc catctacacc accatgctga tctgctacag ccactccaac   10020
gcaaccgtcc attccatcta caccaatgtc catccatccc agccactcca gcacctccaa   10080
ccatcccacc cacccctatgt ctccatccag ccactggtgg ggtgcaggac atggggccag   10140
ctctactgtc aggactgggg ttttgcatg gccccatacc acttctgcag aagagacgca   10200
ctgaaagttt ggctgaccat tttctccgcg gtagagttgt ggcagttctg taatttaggg   10260
tcttttatcc agtttggaga tgggctggga tctcccagct ccatggcagg cattcatgac   10320
actgggttta gtatctgatg ggtgggatgt ggctgaactt cattttcttt ccccagtgac   10380 aaagttttg cagttgaata tgaattcctg cttctgctc tatgagttgt ttttttccca    10440
ggacgtacac agggaatcag cagtcttcat tctccctctg ccatgtgtag actctgccac   10500
acaggactgt gctgtcctca tgcccctgcg cccaaattgt tgccctctgc ccatgcctgc   10560
caagctgagc ccccctgca ggctgccatg ctggattgac atgagccctg agattggtac   10620
agaaatggtg attttggggt tttctctgca ctcaggaagc tgaaggctca atgctcagtg   10680
atggatttac caaactgtgc cctgaggcag ctgctcatgc tggataaagt cactggagca   10740
caggtaacca ggcgctgggc agggatttct catgggcccc acttggaaag ctgcaggctg   10800
caagcctgga cgcctctgcc ttcacgcctc accctcatga ggacaacctc actaattatt   10860
gattaaaaga ttttgctaaa ccatctccag aagcaacaac ccactgagga gcatgtgctg   10920
aattatacat cacagcaccg cggccctgcc ctcatggcag ggctgcatgg cacccacagt   10980
ggcactcaga gggaccacag ggctgagaca gccgggtctg gtggtgggga cacagctgag   11040
cataggatga gccccccggg cagtgctggg cttttgctaat gagcagaagt atggatagaa   11100
agcaacccca gggctccgta cccagctgca gctcttgctc tgtcgtgtcc tttggtgaaa   11160
ctttaaacag tcgcctttt ttttctcttt cttttctggc ttgccattaa tttcaaaccg   11220
agagagacct aatttagtaa atgagatgct tcaggaaggc tttaattagc tgcagatgga   11280
ggcaggcagt gctatcgtgg ggcctggatc gcacaggggg ctgcatatcc tcactagcag   11340
aatacaccca ggctgggtcc ctcccacatt catgccccag accagaggga atatgctctg   11400
ttccccacac atctctccca atcttgcagc cgttgagccc caacatccca ccagcacacg   11460
```

```
gggctcagca cgcctggcga cgtggcatca gcagagcagg ccgcatggta cagctccatc  11520
agcacagctg gggccacaca aagagctggg ttactgtggg cagcaggctg aaacccgaaa  11580
acaagggctg ggggctcaga atagccctgg gagcaggcag ggcctggggg tgagggcaag  11640
caccaggccc agggccacac agcccttcca ggaaggcaca cgcgctgtca gggtgcagca  11700
gctcagcccc accatgcagc tgtgcagccg gggcatcccc aagctaaatt tacttctcag  11760
tctccaatca gaaactgaag ctgaggggcc cacgccggcc aaaaaaagga aacgaaacag  11820
tctccagaaa gcactgacgt gtgaagcaga gcgagcgccg cgcaaaccag ccgccatgtc  11880
acacacctca ggttggggct ttgacagact gagctttgct gctgctcggg gtgggtgccc  11940
acggcctggg cacatgggat ggggtacaca agtacacaca cttgcacacc cacaccccaa  12000
cacttcaggt gatgctggtg cagatgggtg ccccccaggc tgaccccccc acgcgtgggc  12060 ctggcccac actgctccat ccgtgtctct gtccccatgt gccacccctg cccgctccca  12120
ccacgcgtca ccccaaatcc tgagttaatc ccacgactcc tgcctgcttc cagcatccat  12180
ggcagactgg agatgcccaa aatgcagagc aggtttccct gaatctgaga gatgaaatgg  12240
agttatgggt gttccctgc ggcggagccc cagctgtagg aagctcagag ccatcacaca  12300
gcaattaaag aggaattaaa ttaaatcaat aaatgtttta ggcgggctca gctgccagca  12360
ccacctgacc gaaacagccc gcttgcaaag aggagagcat ttgcatggct gtggcaaaac  12420
agcaaccgcc tgttgtgcag ctgggatggt gttatctgga aatgtacgca gcccaggagg  12480
ggtaaacagc tccaaactga gaccccgagc ttgtccacag gttgtaaaca ggctgacata  12540
aacacctttg tgccgtggaa aaatatttat cacctcaaat atagcaggtt aataaaataa  12600
aactcccaac ggagctacac acctgctttg gaagggaagc agacacttgt tttctgcttg  12660
atgttggctg taggaaacca tgtttcccga tgcaggaggg ccacaaagca ctgacaacac  12720
aatgtgagct gagcttcgcc cctgtttaag ccccaccac agggcttgtg gcctcggagc  12780
aggcaggacg caggggtggc accgggctgg gtgacatggg ctggtcctgg ggtgtctcac  12840
tgagctcttt ggggaggggt tggagccctg gggcaatcac agcacacaca gaggaggtgg  12900
ggggatgcag ccagcagctg ccctgcacta agaaaacccc atccgtgggc tttcagatgg  12960
ccttcccatc tctctgcagc ctctgcatgg gctgagcgca aggtttaagt gtttctgcca  13020 tgttttggg catgtttgga ggggcagcgt gggcccgggc atacgggtac cgccacgtgc  13080
tgccagcccc acagctgagc ctgcactctc ccagatgtgc tgaccgcagc cacggggggca  13140 acagtttctc ttgctaaaaa ttgtagccgg gaagaaaaca cgtggcaact tcggccaaac  13200
agcagctgga ggacaggaat agccgtggcc acggcacgct ctgcttcctc ggcacaaaca  13260
ttccagtacg tggcaccacg agcgccgctg cccggcacag cagcaagcag agccaggagc  13320
aggaaatgct gatttgggcc ccatttggc catggctgag agaagaggct tccagggagc  13380
tggtcagctt ggtccccaag ctgtggcttg gggaaatgat ggggaaggga ttgccactgc  13440
ccaccctgca gagcaggctc tggtcccatc tcactgcagg gcaccagggc gtttgcactg  13500
cagcaattca cagaaacacc tgaaatggct cctgtcttgt tcaacatctt catcagtgac  13560
ctggatgagg ggacagcatc caccatcagc gggttcactg atcatatgaa gtcgggaaga  13620
gtggctgacg caccacaagg ctgtgctgcc attcaacagg acgtggacag actggagagc  13680
tggacaggga ggaacccaat gaggttcaac aatggcaagt gtaggatcta cacctgggaa  13740
ggaataacag catgcatcag ttcaggttag gggctgagct gctgcagatg agctctgaga  13800
```

```
gaaggacctg agcgtcctgc tggacagcag gctggctgtg agccaccggt gtgccctggt    13860
ggccaagaag gccagtggta tcctggggag caccgcaatg agtgggca gcagggcgag      13920 ggaggtgagg ctgcatttgg agcaccgtgc ccagttctgg gctcctcagt tcaaggcaga    13980
cagggaactg ctggagagag cccagcagag gggctgcaat gatgatgaag gtcctggagc    14040
atcgcctgta tgaggaaagg ctgagggacc tgggattgtt cagcttggag aagagaagac    14100
tacagggcag gagccaagtg gatagggccg ggctcttttc agcagtgccc attgacaagc    14160
caaggggcag caggcacaaa ctggaacata agaagttcca tctgaacatg aggaaaaact    14220
gcctcgcttt gagggtgtct gagcactgga agaagctgcc cagagaggtg gtggagtctc    14280
ctctggagat attcagagcc tggcaggaca cttttgctg agtaacctac tgtagggaac     14340
ctgacgcagc agaggggtcg gactggagga tctccggagg tctctttcaa cccctacagt    14400
tccatgaaat acctcaaaca ctgccaagcg cagtgctaag gcaagggtaa catttgtaaa    14460
ctgaaacagg gtgggtttaa gttagatgta agaagaaac tcttcactca gagggtggcg     14520
aggccctggc acaggctgcc catggaggct gcgggtgccc catccctggc agtgcccaag    14580
gcaagagccc agcagcgacc acagccccac aaggacgagc gtggcccctc gtatctcagc    14640
tcaccctgcc ccagctcaac ccccacctcc ggcacagcgc gggcacacag ccgggccctg    14700
tgcttatgga gcccttgggg caggtcagca ctcacaccct ccaaacacag ccgtggctcc    14760
caaccggagg cagctggatc tcggcagcca taaccaagca gggccatgcg ggggtgacac    14820
cggggtcccc caccccctgt ggggcagcgt atgggctggg ccctgctcc agtctgcagc     14880 gtgtgcatgg gaaccatcat cagacaccac ctagaccacc cgcagcccta agctgcctca    14940
cagcagggat tgctccgtca caccgtgacc ccgtgccctt attccatcac ttatggggct    15000
gggagtgcct ggaccttggg cacattaacg aggatttccc gctctgccct cgctttgctc    15060
cgagccgtgg ggctgtgtag tgcagacaca gctgcagcct aaaattagca cctgggaaag    15120
gcccccatgc tgcaccgcac agggctgaga tgtgccacgt ccccatggcc ggagctgggg    15180
aaggcaacgt ggccctgtgc gtgtgcacgc tgagcacaag gacacgtgct gggccaggat    15240
ttgtctcccc ggggctcacg ctatgtgtca ccctgtgctg tgccatcccc tcccgcagcc    15300
cccagctccc ccacggccgc acgccgcctg catccctgca acggcaccgc acagagacac    15360
ggagccaggg gccgcacacg gggccaggag ctcacccttta ttgcagccct gacagcccca   15420
cggcccagcc cgcaccgggg ctgccacatc ctcacccgac cgacggcccc agctgctcct    15480
taccatttct tcccccatca cccataaacc agaagccgcc tcaccgctac gcggagcggg    15540
cagcagggaa cccgggccct aaggggaga cgagaggggg ccgagcaggg gcaggaggag     15600
cagcagggcg aggggcagc ggggcaccc acagctggac gtggcatctc gggaggagaa     15660
gaccttgcgg ctgcggagcg gttgtggcgg acggaagttg ttggtcatct tcagggcgc     15720 agcgcccgag gccgggaagt gcacagtgct gacaaacgcc tgcagctgcg gggagagcac    15780
cgcgggcgcc gcagccgtga ggcgtagggc gaagcggggc acacgcgtgg ctgctgccgg    15840
gcagagcgca gcgcaggagc cccgtctttc cccctaccgg cagcacacgg ctctgcacac    15900
accgcgcttc gtgccgcctc gcagccgacg ctgcaggaag cccagccgag cgcttacaga    15960
gcggccggga aatgcatctg ctgaggtgcc cgggcaatgc agaacttcat ccatccccac    16020
atccattcac cagtcccctc ccaaaccccc atgcccatcc ggcgaccac ccaccctcct     16080 cttggtgccc ctctcaagct ctccatcccc acattcctac agatgtcccc tttactttgc    16140
ctgcaaggtg caagaaaacg cacagggacc ggggtgctc acagcacggc tttggccaga    16200
```

```
cgggcccttc catcccatgg cagcagggcc gaggaatccc attacctgct ccctgctgat    16260
gcccacaggc tcctcaaaca cggtccagat gacggcctcg ctgcagtcag ggtggtcag    16320 ggagccctgg tagcggtagt accgggacag ctgtgcaacg tgcggccgcc accgcggtgg    16380
agctccagct tttgttccct ttagtgaggg ttaattgcgc gcttggcgta atcatggtca    16440
tagctgtttc ctgtgtgaaa ttgttatccg ctcacaattc cacacaacat acgagccgga    16500
agcataaagt gtaaagcctg gggtgcctaa tgagtgagct aactcacatt aattgcgttg    16560
cgctcactgc ccgctttcca gtcgggaaac ctgtcgtgcc agctgcatta atgaatcggc    16620
caacgcgcgg ggagaggcgg tttgcgtatt gggcgctctt ccgcttcctc gctcactgac    16680
tcgctgcgct cggtcgttcg gctgcggcga gcggtatcag ctcactcaaa ggcggtaata    16740
cggttatcca cagaatcagg ggataacgca ggaaagaaca tgtgagcaaa aggccagcaa    16800
aaggccagga accgtaaaaa ggccgcgttg ctggcgtttt tccataggct ccgcccccct    16860
gacgagcatc acaaaaatcg acgctcaagt cagaggtggc gaaacccgac aggactataa    16920
agataccagg cgtttccccc tggaagctcc ctcgtgcgct ctcctgttcc gaccctgccg    16980
cttaccggat acctgtccgc ctttctccct tcgggaagcg tggcgctttc tcatagctca    17040
cgctgtaggt atctcagttc ggtgtaggtc gttcgctcca agctgggctg tgtgcacgaa    17100
ccccccgttc agcccgaccg ctgcgcctta tccggtaact atcgtcttga gtccaacccg    17160
gtaagacacg acttatcgcc actggcagca gccactggta acaggattag cagagcgagg    17220
tatgtaggcg gtgctacaga gttcttgaag tggtggccta actacggcta cactagaagg    17280
acagtatttg gtatctgcgc tctgctgaag ccagttacct tcggaaaaag agttggtagc    17340
tcttgatccg gcaaacaaac caccgctggt agcggtggtt tttttgtttg caagcagcag    17400
attacgcgca gaaaaaaagg atctcaagaa gatcctttga tcttttctac ggggtctgac    17460
gctcagtgga acgaaaactc acgttaaggg attttggtca tgagattatc aaaaaggatc    17520
ttcacctaga tccttttaaa ttaaaaatga agttttaaat caatctaaag tatatatgag    17580
taaacttggt ctgacagtta ccaatgctta atcagtgagg cacctatctc agcgatctgt    17640
ctatttcgtt catccatagt tgcctgactc cccgtcgtgt agataactac gatacgggag    17700
ggcttaccat ctggccccag tgctgcaatg ataccgcgag acccacgctc accggctcca    17760
gatttatcag caataaacca gccagccgga agggccgagc gcagaagtgg tcctgcaact    17820
ttatccgcct ccatccagtc tattaattgt tgccgggaag ctagagtaag tagttcgcca    17880
gttaatagtt tgcgcaacgt tgttgccatt gctacaggca tcgtggtgtc acgctcgtcg    17940
tttggtatgg cttcattcag ctccggttcc caacgatcaa ggcgagttac atgatccccc    18000
atgttgtgca aaaaagcggt tagctccttc ggtcctccga tcgttgtcag aagtaagttg    18060
gccgcagtgt tatcactcat ggttatggca gcactgcata attctcttac tgtcatgcca    18120
tccgtaagat gcttttctgt gactggtgag tactcaacca agtcattctg agaatagtgt    18180
atgcggcgac cgagttgctc ttgcccggcg tcaatacggg ataataccgc gccacatagc    18240
agaactttaa aagtgctcat cattggaaaa cgttcttcgg ggcgaaaact ctcaaggatc    18300
ttaccgctgt tgagatccag ttcgatgtaa cccactcgtg cacccaactg atcttcagca    18360
tcttttactt tcaccagcgt ttctgggtga gcaaaaacag gaaggcaaaa tgccgcaaaa    18420
aagggaataa gggcgacacg gaaatgttga atactcatac tcttcctttt tcaatattat    18480
tgaagcattt atcagggtta ttgtctcatg agcggataca tatttgaatg tatttagaaa    18540
aataaacaaa taggggttcc gcgcacattt ccccgaaaag tgccac               18586
```

```
<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 6
cagtgtccaa attccttaaa tttcc                                           25

<210> SEQ ID NO 7
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 7
atacgatgtt ccagattacg ctt                                             23

<210> SEQ ID NO 8
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 8
tgaacccata aagtgaaatc ctc                                             23

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 9
ttcggtcccg tggcccat                                                   19

<210> SEQ ID NO 10
<211> LENGTH: 22
<212> TYPE: DNA
<213> ORGANISM: artificial sequence
<220> FEATURE:
<223> OTHER INFORMATION: Synthetic oligonucleotide

<400> SEQUENCE: 10
ggaacacggc ggcatcagag ca                                              22

<210> SEQ ID NO 11
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 11
ccggaaagca aaatttgggg gcaa                                            24

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide
```

<400> SEQUENCE: 12

```
gggggttcgg tgcagttttt c                                              21
```

<210> SEQ ID NO 13
<211> LENGTH: 23
<212> TYPE: DNA
<213> ORGANISM: artificial sequence
<220> FEATURE:
<223> OTHER INFORMATION: Synthetic oligonucleotide

<400> SEQUENCE: 13

```
atattggccc catttcccct cag                                            23
```

<210> SEQ ID NO 14
<211> LENGTH: 14762
<212> TYPE: DNA
<213> ORGANISM: artificial sequence
<220> FEATURE:
<223> OTHER INFORMATION: Synthetic vector construct

<400> SEQUENCE: 14

```
ctaaattgta agcgttaata ttttgttaaa attcgcgtta aatttttgtt aaatcagctc      60
attttttaac caataggccg aaatcggcaa atcccttat aaatcaaaag aatagaccga     120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300
cccccgattt agagcttgac ggggaaagcc ggcgaacgtg gcgagaaagg aagggaagaa    360
agcgaaagga gcggcgcta gggcgctggc aagtgtagcg gtcacgctgc gcgtaaccac     420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat gggtaccgg     660
cgcgcctggg aaatttggcc ctcttggccc aattttgccc aaaaatggca aaatttgggg    720
tcatttcttc cccgtaggt gagagcttca acctccagca gctccacgac tccaaaaaag     780
agacattttg cccattttct gccatttttt gacccaaatt tgggtgtctt ttccccttcc    840
acggccactt tgaaaccta caaattactg cctcttttt tctccgtttt ttgccccaaa      900
tctgcctttt tttccccct ttttggggcc ctccgggagg aaacgtctcc accggtggcc     960
gctcaagtgg tgaacccaca aactttgggg taaaaacaca ggattttggt caacgttgta   1020
tcactgtggg ttgtagtgct tacggttgtg gtgcttatca cggtgctcca tcccataaca   1080
aaaaccatcc tcattttggg gcaactttgg ccctttttgg tcaatttttg cccccacgt    1140
acgacgattt ccccctcttc tttggccacc attgacccaa aatttggggt tattttcccc   1200
cttttttacca atattaccaa aaaaaaatca attttttccca tcttccccag accacaaaat 1260
tgggattttt ttttggcctt tttcggctat tttttgcccc aaaatccaac gattccctc    1320
tcctcctcac ctccaaaaat ggggccattt tgtccctttt ccccattttc caccccctt    1380
ccccccctc tccacattta cagttttgg acgctcccaa tcttgccccg ttttgcccca     1440
aaatcccct ctttccaggc attcgatccc aaaattgaga tatttgatca ttttttaacca   1500
ttttccccca aaataccgcc tcctcactga cggccgcgt gccaaaaacg ggaattttc     1560
tcccaaatac gttcaatgtt ttcccttttt tgcccgtttt ttgaccggtt ttgcccattt   1620
```

```
ttgtgcgttt taaccatttt tttttacat tttttaacca aatttgtgtg ttttacctt      1680 aagattcagc tcccatgggt gaaaaatgag aggtttctcc ccattcaaat tctacgactt    1740
ttgggatatc cctacgtgga gaatttgggg taaaaatgcc acaaatcggt taaaaatggc    1800
attttttggc taaaaatgg cattttttgt tctgaaaata gcatttttg gctaaaattg      1860 ggggttttag ccctaaaata gggaggaaaa caatgaggat ttgaaacact ccgtccccaa    1920
aattgaaatc tttgattctg gcatcattgg gtgatccgaa gtgaggaatt tgggggtaaaa  1980 atggctcaaa ttggttaaaa ataaccgttt ttggtctgaa aatggcattt ttttggctaa   2040 aattgggggtt tttagcccta aaatagggag gaaaacagtg aggatttgaa aactctgaac  2100
ccataaagtg aaatcctcaa ttttgggcat cattgggtga tcttaaggga ggaatttggg   2160
gcaaaaatgg ccaaattggt taagaatagc agttttggt ctaaaaatgg catttttgg     2220 ctaaaattgg ggtttttagc cctaaaatgg ggaggaatcc aatgaggatt tgaaacactc   2280
cgagcccaga attgaaatct tcgattttgt tcatctttgg gtgattctaa cggaggaatt   2340 tgggggtaaaa acagcccaaa ttggttaaaa atggcagttt ttggtctaaa aatggcagtt  2400
tttgttctga aaatggcatt ttttggctaa aattgggggtt tttgcccta aaatagtgag   2460 gaaaacaaca aggatttgaa aaacctgaag gcaaacaatg aaatcttcga ttttgggcca   2520
atattgcagg aatttggagc gaaggatggc caaaaacgg ttgttttttt cttttttaac    2580
caaaatgggc ggttttcgcc ccgagctagc ataacttcgt atagcataca ttatacgaag   2640
ttataagcgt aatctggaac atcgtatgta ccggatccga agcaggcttt cctggaaggt   2700 cctgaaggg ggcgtccgcg ggagctcacg ggacagcccc cccccaaag ccccagggga     2760 tgtaattacg tccctccccc gctaggggc agcagcgagc cgcccggggc tccgctccgg    2820
tccggcgctc ccccgcatc cccgagccgg cagcgtgcgg ggacagcccg ggcacgggga    2880
aggtggcacg ggatcgcttt cctctgaacg cttctcgctg ctctttgagc ctgcagacac   2940 ctgggggat acgggaaaa agctttaggc tgagaagcag gctttcctgg aaggtcctgg     3000
aagggggcgt ccgcgggagc tcacggggac agcccccccc caaagccccc agggatgtaa   3060
ttacgtccct ccccgctag ggggcagcag cgagccgccc ggggctccgc tccggtccgg    3120 cgctccccc gcatcccga ccggcagcg tgcgggaca gcccgggcac ggggaaggtg       3180
gcacgggatc gctttcctct gaacgcttct cgctgctctt tgagcctgca gacacctggg   3240
gggatacggg gaaaagctt taggctgaac tagctagtct cgaggtcgag gtgagcccca    3300
cgttctgctt cactctcccc atctccccc cctcccacc cccaattttg tatttattta     3360 tttttaatt attttgtgca gcgatggggg cggggggggg ggggcgcgc gccaggcggg     3420 gcggggcggg gcgaggggcg gggcggggcg aggcggagag gtgcggcggc agccaatcag   3480
agcggcgcgc tccgaaagtt tccttttatg gcgaggcggc ggcggcggcg gccctataaa   3540
aagcgaagcg cgcggcgggc gggagtcgct gcgttgcctt cgcccgtgc cccgctccgc    3600 gccgcctcgc gccgcccgcc ccggctctga ctgaccgcgt tactcccaca ggtgagcggg   3660
cgggacggcc cttctcctcc gggctgtaat tagcgcttgg tttaatgacg gctcgtttct   3720
tttctgtggc tgcgtgaaag ccttaaaggg ctccggagg gcccttgtg cggggggag      3780 cggctcgggg ggtgcgtgcg tgtgtgtgtg cgtggggagc gccgcgtgcg gccgcgctg    3840 cccggcggct gtgagcgctg cgggcgcggc gcgggctttt gtgcgctccg cgtgtgcgcg   3900
aggggagcgc ggccggggc ggtgcccgcg ggtgcggggg gctgcgagg gaacaaagg      3960 ctgcgtgcgg ggtgtgtgcg tggggggtg agcagggggt gtgggcgcgg cggtcgggct   4020
```

```
gtaaccccc cctgcacccc cctccccgag ttgctgagca cggcccggct tcgggtgcgg   4080
ggctccgtgc ggggcgtggc gcggggctcg ccgtgccggg cggggggtgg cggcaggtgg   4140
gggtgccggg cggggcgggg ccgcctcggg ccggggaggg ctcggggag gggcgcggcg    4200 gccccggagc gccggcggct gtcgaggcgc ggcgagccgc agccattgcc ttttatggta   4260
atcgtgcgag agggcgcagg gacttccttt gtcccaaatc tggcggagcc gaaatctggg   4320
aggcgccgcc gcaccccctc tagcgggcgc gggcgaagcg gtgcggcgcc ggcaggaagg   4380
aaatgggcgg ggagggcctt cgtgcgtcgc cgcgccgccg tcccttctc catctccagc    4440 ctcggggctg ccgcagggg acggctgcct tcgggggga cggggcaggg cggggttcgg     4500
cttctggcgt gtgaccggcg gctctagagc ctctgctaac catgttcatg ccttcttctt   4560
tttcctacag ctcctgggca acgtgctggt tgttgtgctg tctcatcatt ttggcaaaga   4620
attatcgcat gcctgcgtcg acggtaccgc gggcccggga tccaccggtc gccaccatgg   4680
tgagcaaggg cgaggagctg ttcaccgggg tggtgcccat cctggtcgag ctggacggcg   4740
acgtaaacgg ccacaagttc agcgtgtccg gcgagggcga gggcgatgcc acctacggca   4800
agctgaccct gaagttcatc tgcaccaccg gcaagctgcc cgtgccctgg cccacccct cg  4860 tgaccaccct gacctacggc gtgcagtgct tcagccgcta ccccgaccac atgaagcagc   4920
acgacttctt caagtccgcc atgcccgaag ctacgtcca ggagcgcacc atcttcttca    4980
aggacgacgg caactacaag acccgcgccg aggtgaagtt cgaggcgac accctggtga   5040 accgcatcga gctgaagggc atcgacttca aggaggacgg caacatcctg ggcacaagc    5100 tggagtacaa ctacaacagc cacaacgtct atatcatggc cgacaagcag aagaacggca   5160
tcaaggtgaa cttcaagatc cgccacaaca tcgaggacgg cagcgtgcag ctcgccgacc   5220
actaccagca gaacaccccc atcggcgacg gccccgtgct gctgcccgac aaccactacc   5280
tgagcaccca gtccgccctg agcaaagacc ccaacgagaa gcgcgatcac atggtcctgc   5340
tggagttcgt gaccgccgcc gggatcactc tcggcatgga cgagctgtac aagtaaagcg   5400
gccggccgcg actctagatc ataatcagcc ataccacatt tgtagaggtt ttacttgctt   5460
taaaaaacct cccacacctc cccctgaacc tgaaacataa aatgaatgca attgttgttg   5520
ttaacttgtt tattgcagct tataatggtt acaaataaag caatagcatc acaaatttca   5580
caaataaagc atttttttca ctgcattcta gttgtggttt gtccaaactc atcaatgtat   5640
cttaaggaac cccttcctcg acattgatta ttgactagct agttattaat agtaatcaat   5700
tacggggtca ttagttcata gcccatatat ggagttccgc gttacataac ttacggtaaa   5760
tggcccgcct ggctgaccgc ccaacgaccc cgcccattg acgtcaataa tgacgtatgt    5820
tcccatagta acgccaatag ggactttcca ttgacgtcaa tgggtggact atttacggta   5880
aactgcccac ttggcagtac atcaagtgta tcatatgcca agtacgcccc ctattgacgt   5940
caatgacggt aaatggcccg cctggcatta tgcccagtac atgaccttat ggactttcc    6000 tacttggcag tacatctacg tattagtcat cgctattacc atgggtcgag gtgagcccca   6060
cgttctgctt cactctcccc atctccccc cctccccacc cccaattttg tatttattta    6120 tttttttaatt attttgtgca gcgatggggg cggggggggg ggggcgcgc gccaggcggg   6180 gcggggcggg gcgaggggcg gggcggggcg aggcggagag gtgcggcggc agccaatcag   6240 agcgcgcgc tccgaaagtt tccttttatg gcgaggcggc ggcggcggcg gccctataaa    6300
aagcgaagcg cgcggcgggc gggagtcgct gcgttgcctt cgccccgtgc cccgctccgc   6360
```

-continued

```
gccgcctcgc gccgcccgcc ccggctctga ctgaccgcgt tactcccaca ggtgagcggg   6420
cgggacggcc cttctcctcc gggctgtaat tagcgcttgg tttaatgacg gctcgtttct   6480
tttctgtggc tgcgtgaaag ccttaaaggg ctccgggagg gcccttttgtg cgggggggag   6540
cggctcgggg ggtgcgtgcg tgtgtgtgtg cgtggggagc gccgcgtgcg gcccgcgctg   6600
cccggcggct gtgagcgctg cgggcgcggc gcggggcttt gtgcgctccg cgtgtgcgcg   6660
aggggagcgc ggccggggc ggtgcccgc ggtgcggggg ggctgcgagg ggaacaaagg   6720
ctgcgtgcgg ggtgtgtgcg tgggggggtg agcagggggt gtgggcgcgg cggtcgggct   6780
gtaacccccc cctgcacccc cctccccgag ttgctgagca cggcccggct tcgggtgcgg   6840
ggctccgtgc ggggcgtggc gcggggctcg ccgtgccggg cggggggtgg cggcaggtgg   6900
gggtgccggg cggggcgggg ccgcctcggg ccggggaggg ctcggggag gggcgcggcg   6960
gccccggagc gccggcggct gtcgaggcgc ggcgagccgc agccattgcc ttttatggta   7020
atcgtgcgag agggcgcagg gacttccttt gtcccaaatc tggcggagcc gaaatctggg   7080
aggcgccgcc gcaccccctc tagcgggcgc gggcgaagcg gtgcggcgcc ggcaggaagg   7140
aaatgggcgg ggagggcctt cgtgcgtcgc cgcgccgccg tccccttctc catctccagc   7200
ctcggggctg ccgcagggg acggctgcct tcgggggga cggggcaggg cggggttcgg   7260
cttctggcgt gtgaccggcg gctctagagc ctctgctaac catgttcatg ccttcttctt   7320
tttcctacag ctcctgggca acgtgctggt tattgtgctg tctcatcatt ttggcaaaga   7380
attcctagcg ccaccatgac cgagtacaag cctaccgtgc cctggccac tcgcgatgat   7440
gtgccccgcg ccgtccgcac tctggccgcc gctttcgccg actacccgc tacccggcac   7500
accgtggacc ccgaccggca catcgagcgt gtgacagagt tgcaggagct gttcctgacc   7560
cgcgtcgggc tggacatcgg caaggtgtgg gtagccgacg acggcgcggc cgtggccgtg   7620
tggactaccc ccgagagcgt tgaggccggc gccgtgttcg ccgagatcgg ccccgaatg   7680
gccgagctga gcggcagccg cctggccgcc agcagcaaa tggagggcct gcttgccccc   7740
catcgtccca aggagcctgc ctggtttctg gccactgtag gagtgagccc cgaccaccag   7800
ggcaagggct tgggcagcgc cgtcgtgttg cccggcgtag aggccgccga acgcgccggt   7860
gtgcccgcct ttctcgaaac aagcgcacca agaaaccttc cattctacga gcgcctgggc   7920
ttcaccgtga ccgccgatgt cgaggtgccc gagggaccta ggacctggtg tatgacacga   7980
aaacctggcg cctaatgatc tagaaccggt catggccgca ataaaatatc tttatttca   8040
ttacatctgt gtgttggttt tttgtgtgtt cgaacctgca gcccggggga tccgaagcag   8100
gctttcctgg aaggtcctgg aagggggcgt ccgcgggagc tcacggggac agccccccc   8160
caaagccccc agggatgtaa ttacgtccct cccccgctag ggggcagcag cgagccgccc   8220
ggggctccgc tccggtccgg cgctcccccc gcatccccga gccggcagcg tgcgggaca   8280
gcccgggcac ggggaaggtg gcacgggatc gctttcctct gaacgcttct cgctgctctt   8340
tgagcctgca gacacctggg gggatacggg gaaaaagctt taggctgaga agcaggcttt   8400
cctggaaggt cctggaaggg ggcgtccgcg ggagctcacg ggacagcccc cccccaaag   8460
cccccaggga tgtaattacg tccctccccc gctaggggc agcagcgagc cgccggggc   8520
tccgctccgg tccggcgctc ccccgcatc cccgagccgg cagcgtgcgg ggacagcccg   8580
ggcacgggga aggtgcacg ggatcgcttt cctctgaacg cttctcgctg ctctttgagc   8640
ctgcagacac ctggggggat acggggaaaa agcttaggc tgaactagaa tgcatataac   8700
ttcgtatagc atacattata cgaagttatg gatcccccaa atcaatctaa agtatatatg   8760
```

-continued

```
agtaacctga ggctatggca gggcctgccg ccccgacgtt ggctgcgagc cctgggcctt      8820
cacccgaact tgggggtgg ggtggggaaa aggaagaaac gcgggcgtat tggccccaat       8880
ggggtctcgg tggggtatcg acagagtgcc agccctggga ccgaacccccg cgtttatgaa     8940 caaacgaccc aacaccgtgc gttttattct gtcttttat tgccgtcata gcgcgggttc       9000
cttccggtat tgtctccttc cgtgtttcag ttagcctccc cctagggtgg gcgaagaact      9060
ccagcatgag atccccgcgc tggaggatca tccagccggc gtcccggaaa acgattccga      9120
agcccaacct ttcatagaag gcggcggtgg aatcgaaatc tcgtgatggc aggttgggcg      9180
tcgcttggtc ggtcatttcg aaccccagag tcccgctcag aagaactcgt caagaaggcg      9240
atagaaggcg atgcgctgcg aatcgggagc ggcgataccg taaagcacga ggaagcggtc      9300
agcccattcg ccgccaagct cttcagcaat atcacgggta gccaacgcta tgtcctgata      9360
gcggtccgcc acacccagcc ggccacagtc gatgaatcca gaaaagcggc cattttccac      9420
catgatattc ggcaagcagg catcgccatg ggtcacgacg agatcctcgc cgtcgggcat      9480
gctcgccttg agcctggcga acagttcggc tggcgcgagc ccctgatgct cttcgtccag      9540
atcatcctga tcgacaagac cggcttccat ccgagtacgt gctcgctcga tgcgatgttt      9600
cgcttggtgg tcgaatgggc aggtagccgg atcaagcgta tgcagccgcc gcattgcatc      9660
agccatgatg gatactttct cggcaggagc aaggtgagat gacaggagat cctgccccgg      9720
cacttcgccc aatagcagcc agtcccttcc cgcttcagtg acaacgtcga gcacagctgc      9780
gcaaggaacg cccgtcgtgg ccagccacga tagccgcgct gcctcgtctt gcagttcatt      9840
cagggcaccg gacaggtcgg tcttgacaaa aagaaccggg cgcccctgcg ctgacagccg      9900
gaacacggcg gcatcagagc agccgattgt ctgttgtgcc cagtcatagc cgaatagcct      9960
ctccacccaa gcggccggag aacctgcgtg caatccatct tgttcaatca tgcgaaacga     10020
tcctcatcct gtctcttgat cgattacgcc cccaactgag agaactcaaa ggttaccccca    10080 gttggggcac actagtggcg gtctgagggg aaaatgtcgt tttggggcca ttttgggcca     10140
tttgagggga aatttgggtc aaaaaatgac gattttgggt cattttaggg ataaaaaatg     10200
aatttaggga gatttgaggg caaatttggg tcaaaaaatg gtgatttggg gtcaaaaatg     10260
gacaattttg ggtcatttta gggttaaaaa tggatttagg gaaatttgat ggcaaatttg     10320
ggtcaaaaaa tggtgatttt gggtcaaaaa atgattattt tgggtcattt tagggagaaa    10380
aatgaattta gggagatttg agggcaaatt tgggtcgaaa aatggtgatt ttgggtgaaa     10440 aatgacaat tttgggtcat tttagggtta aaaatgaatt tagggagatt ggacggcaaa      10500
tttgggtcaa aaatggtga tttggggtca aaaataatt attttgggtc attttaggga       10560
taaaaaatga atttagggag atttgagggc aaatttgggt cgaaaaatgg tgattttggg     10620
tgaaaaatgg acaattttgg gtcattttag ggataaaaaa tgaatttagg gcgatttgag     10680
ccaaatttgg gtcaaaaatg gtgatttttgg gtgaaaaatt gacagttttg ggtcatttta    10740
gggttaaaaa tgaatttagg gagattggac ggcaaatttg ggtcaaaaaa tggtgatttg     10800
ggtcaaaaaa atgattattt tgggtcattt tagggataaa aatgaatttt agggagatgt     10860
gagggcaaat ttgggtcgaa aaatggtgat tttgggtgaa aaattgacag ttttgggtca     10920 ttttaggat ataaatggac ttagagagat ttgagggcaa atttgggtga aaaatggac       10980 aatttggtc atttttggga tataaatgaa tttaagattt gacggcaaat ttgggtcaaa      11040
aaatggtgat ttgggtcaaa aatggtgatt ttggttgaaa aacggccatt ttgggtcatt    11100
ttagggataa aaatgaattt agggagattt gagggcaaat ttgggtgaaa aagggcgat     11160
```

```
ttggggtca ttttagggag aaaaatgaat ttagggcgat tgagggcaa atttgggtga   11220 aaaaagggag atttttggtc attttaggga taaaaatgaa tttagggaga actgagggca   11280
aatttgggtc aaaaaatgac aatttgggtc gttctaggga gaaaaatgaa ttttgggcga   11340
tttgagggta aatttgggtc gaaaaatggt gatttgggtc aaaaaatgat tattttgggt   11400
catttaaggg agaaaaggga tttagggaga tttgagggca aatttgggtc gaaaaattgt   11460
gatttggggt caaaaaatga caattttggg tcattttagg gatataaatg gacttagagc   11520
gatttgaggg caaatttggg tgaaaaaatg acaatttggg tcattttagg gatataaatg   11580
aatttagggc gatttgaggg caaatttggt tcgaaaatgg tgattttggg tcaatttagg   11640
gaggaaaatg aatttaaggc aatttgaagg caaatttggg tgaaaaatg acaatttggg    11700 gtcattttaa agataaaatg aatttagggc tatttgaggg caaatttggg tcaaaaaatg   11760
gtgatttggg gtcaaaaaat atggtgattt tgagtcgttt tagggggggaa aatgaattta   11820 gggagatttg agggcaaatt tgggtcaaaa aatggtgatt tttggtcgtt ttagtgataa   11880
aaaatgaatt tagggcagtt tgagggcaaa tctgggtcaa aaaagggtga ttttgagtca   11940
aaaatagtga ttttgggtca ttttagggat ataaatgaat tcagggagat tgagggcaa    12000 atttgagtca aaaatagtga tatggtcaa aagtggtgat tttggttgaa aaacagtcat    12060
tttgggtcat tttagggatt aaaatgaact tagggagatt tgagggcaaa tttgggtcaa   12120
aaaatgacaa ttttgggtca ctttacgaat taaaatgaat tcagggagat tgagggcaa    12180 atttgggtca aaaaatggt gattttgggt cattttaggg ttaaaaatga attcaggatg    12240
atttgaaggc aactttgggt caaaaaaatg attatttggg tcattttaaa gaggaaaatg   12300
aatttaggga gatttgaggg caaattcggg tgaaaattgg acaattttgg gtcattttag   12360
ggataaaaat gaatttaggg agatttgagg gcaaatttgg gtcaaaaaat ggtgattttg   12420
ggtcgtttta ggaataaaaa tgaatttagg gagatttgag gcaaatttg gtcaaaaaa    12480 tggtgatttg gggtcatttt cagaaggaaa atgattattt tccccactaa aaatgtagcg   12540
gccgccaccg cggtggagct ccagcttttg ttcccctttag tgagggttaa ttgcgcgctt   12600
ggcgtaatca tggtcatagc tgtttcctgt gtgaaattgt tatccgctca caattccaca   12660
caacatacga gccggaagca taaagtgtaa agcctggggt gcctaatgag tgagctaact   12720
cacattaatt gcgttgcgct cactgcccgc tttccagtcg ggaaacctgt cgtgccagct   12780
gcattaatga atcggccaac gcgcggggag aggcggtttg cgtattgggc gctcttccgc   12840
ttcctcgctc actgactcgc tgcgctcggt cgttcggctg cggcgagcgg tatcagctca   12900
ctcaaaggcg gtaatacggt tatccacaga atcagggggat aacgcaggaa agaacatgtg   12960
agcaaaaggc cagcaaaagg ccaggaaccg taaaaaggcc gcgttgctgg cgttttttcca   13020 taggctccgc ccccctgacg agcatcacaa aaatcgacgc tcaagtcaga ggtggcgaaa   13080
cccgacagga ctataaagat accaggcgtt ccccctgga agctccctcg tgcgctctcc    13140
tgttccgacc ctgccgctta ccggatacct gtccgccttt ctcccttcgg gaagcgtggc   13200
gctttctcat agctcacgct gtaggtatct cagttcggtg taggtcgttc gctccaagct   13260
gggctgtgtg cacgaacccc ccgttcagcc cgaccgctgc gccttatccg gtaactatcg   13320
tcttgagtcc aacccggtaa gacacgactt atcgccactg gcagcagcca ctggtaacag   13380
gattagcaga gcgaggtatg taggcggtgc tacagagttc ttgaagtggt ggcctaacta   13440
cggctacact agaaggacag tatttggtat ctgcgctctg ctgaagccag ttaccttcgg   13500
aaaaagagtt ggtagctctt gatccggcaa acaaaccacc gctggtagcg gtggtttttt   13560
```

-continued

| | |
|---|---|
| tgtttgcaag cagcagatta cgcgcagaaa aaaaggatct caagaagatc ctttgatctt | 13620 |
| ttctacgggg tctgacgctc agtggaacga aaactcacgt taagggattt tggtcatgag | 13680 |
| attatcaaaa aggatcttca cctagatcct tttaaattaa aaatgaagtt ttaaatcaat | 13740 |
| ctaaagtata tatgagtaaa cttggtctga cagttaccaa tgcttaatca gtgaggcacc | 13800 |
| tatctcagcg atctgtctat ttcgttcatc catagttgcc tgactccccg tcgtgtagat | 13860 |
| aactacgata cgggagggct taccatctgg ccccagtgct gcaatgatac cgcgagaccc | 13920 |
| acgctcaccg gctccagatt tatcagcaat aaaccagcca gccggaaggg ccgagcgcag | 13980 |
| aagtggtcct gcaactttat ccgcctccat ccagtctatt aattgttgcc gggaagctag | 14040 |
| agtaagtagt tcgccagtta atagtttgcg caacgttgtt gccattgcta caggcatcgt | 14100 |
| ggtgtcacgc tcgtcgtttg gtatggcttc attcagctcc ggttcccaac gatcaaggcg | 14160 |
| agttacatga tcccccatgt tgtgcaaaaa agcggttagc tccttcggtc ctccgatcgt | 14220 |
| tgtcagaagt aagttggccg cagtgttatc actcatggtt atggcagcac tgcataattc | 14280 |
| tcttactgtc atgccatccg taagatgctt ttctgtgact ggtgagtact caaccaagtc | 14340 |
| attctgagaa tagtgtatgc ggcgaccgag ttgctcttgc ccggcgtcaa tacgggataa | 14400 |
| taccgcgcca catagcagaa cttttaaaagt gctcatcatt ggaaaacgtt cttcggggcg | 14460 |
| aaaactctca aggatcttac cgctgttgag atccagttcg atgtaaccca ctcgtgcacc | 14520 |
| caactgatct tcagcatctt ttactttcac cagcgtttct gggtgagcaa aaacaggaag | 14580 |
| gcaaaatgcc gcaaaaaagg gaataagggc gacacggaaa tgttgaatac tcatactctt | 14640 |
| ccttttcaa tattattgaa gcatttatca gggttattgt ctcatgagcg gatacatatt | 14700 |
| tgaatgtatt tagaaaaata acaaataggg gttccgcgc acatttcccc gaaaagtgcc | 14760 |
| ac | 14762 |

<210> SEQ ID NO 15
<211> LENGTH: 9736
<212> TYPE: DNA
<213> ORGANISM: Gallus gallus

<400> SEQUENCE: 15

| | |
|---|---|
| cagtgtccaa attccttaaa tttcctcatt tttgcccatt tgccccgaa ataccacacc | 60 |
| cttaatgccc tccggcccc ccccagaatg gagcatttta cactttttgc ccattttgc | 120 |
| tcaaattttg cgtgttttcc tgcggttttg gtcagcgact ctttgaacgt tggggatatt | 180 |
| ttgccatttt ttgatgtttt tgcccaaaat ggaaatattt cgctctcact ctcaacgtcc | 240 |
| ccccaaaaaa tgggctattt tccccatttt cccccatttt ttttatcgaa atcaccgtta | 300 |
| tttctacgaa attttcaccg catttcacaa cgatgggaaa tttggccctc ttggcccaat | 360 |
| tttgcccaaa aatggcaaaa tttggggtca tttcttcccc cgtaggtgag agcttcaacc | 420 |
| tccagcagct ccacgactcc aaaaaagaga catttttgccc attttctgcc atttttttgac | 480 |
| ccaaattttg gggtcttttc cccttccacg gccactttga aaccctacaa attactgcct | 540 |
| cttttttttct ccgttttttg ccccaaatct gccttttttt cccccctttt tggggccctc | 600 |
| cgggaggaaa cgtctccacc ggtggccgct caagtggtga acccacaaac tttggggtaa | 660 |
| aaacacagga ttttggtcaa cgttgtatca ctgtggggttg tagtgcttac ggttgtggtg | 720 |
| cttatcacgg tgctccatcc cataacaaaa accatcctca ttttggggca actttggccc | 780 |
| tttttggtca atttttgccc cccacgtacg acgatttccc cctcttctttt ggccaccatt | 840 |
| gacccaaaat ttggggttat tttcccccctt tttaccaata ttaccaaaaa aaaatcaatt | 900 |

```
tttcccatct tccccagacc acaaaattgg gattttttt  tggccttttt  cggctatttt   960
ttgccccaaa atccaacgat tccctctcc  tcctcacctc caaaaatggg gccattttgt  1020
ccctttccc  cattttccac cccctttccc ccccctctcc acatttacag ttttttggacg 1080
ctcccaatct tgcccgtttt tgccccaaaa tcccctctt  tccaggcatt cgatcccaaa  1140
attgagatat ttgatcattt ttaaccattt tcccccaaaa taccgcctcc tcactgacgg  1200
ccgcggtgcc aaaaacgggg aattttctcc caaatacgtt caatgttttc ccttttttg   1260
cccgttttg  accggttttg cccatttttg tgcgtttta  accatttttt tttacatttt  1320
ttaaccaaat ttgtgtgttt ttaccttaag attcagctcc catgggtgaa aaatgagagg  1380
tttctcccca ttcaaattct acgacttttg ggatatccct acgtggagaa tttggggtaa  1440
aaatgccaca aatcggttaa aaatggcatt ttttggctaa aaaatggcat tttttgttct  1500
gaaaatagca ttttttggct aaaattgggg gttttagccc taaaataggg aggaaaacaa  1560
tgaggatttg aaacactccg tccccaaaat tgaaatcttt gattctggca tcattgggtg  1620
atccgaagtg aggaatttgg ggtaaaaatg gctcaaattg gttaaaaata accgttttg   1680
gtctgaaaat ggcattttt  tggctaaaat tggggttttt agccctaaaa tagggaggaa  1740
aacagtgagg atttgaaaac tctgaaccca taaagtgaaa tcctcaattt tgggcatcat  1800
tgggtgatct taaggagga  atttggggca aaaatggcca aattggttaa gaatagcagt  1860
ttttggtcta aaaatggcat ttttggcta  aaattgggt  tttagccct  aaatggga    1920
ggaatccaat gaggatttga aacactccga gcccagaatt gaaatcttcg attttggtca  1980
tctttgggtg attctaacgg aggaatttgg ggtaaaaaca gcccaaattg gttaaaaatg  2040
gcagttttg  gtctaaaaat ggcagttttt gttctgaaaa tggcattttt tggctaaaat  2100
tggggttttt tgccctaaaa tagtgaggaa acaacaagg  atttgaaaaa cctgaaggca  2160
aacaatgaaa tcttcgattt tgggccaata ttgcaggaat ttggagcgaa ggatggccaa  2220
aaaacggttg ttttttctt  ttttaaccaa aatgggcggt tttcgccccg aaaagagtgg  2280
gtggagtttt tgggtgaaaa aaggcggatt ttgggcatt  gtggtactgc tggtagcatc  2340
gacgcatggg gccacgggac cgaagtcatc gtctcctccg gtgagtcttc aaccccccca  2400
aaactgccgc ggcgattttg gggcaaaatc gggcgatttt gggtcagtcg aagggggcgg  2460
tcggtccatc atttgggcc  gggtgatttt tggggccgaa aagtgggaat ttggggccca  2520
atttggggcc caatttgggg ccaaatttgg gttttcgagg ggggattttt ttaggggagg  2580
attttgggtc cccggagggg ttttggggtg gaaaatggg  gattttgggt cgttttgagg  2640
tggggttttt tggggtagaa atggcggtct gagggggaaaa tgtcgttttg gggccatttt  2700
gggccatttg agggaaatt  tgggtcaaaa aatgacgatt ttgggtcatt ttagggataa  2760
aaaatgaatt taggagatt  tgaggcaaa  tttgggtcaa aaaatggtga tttggggtca  2820
aaaatggaca atttttgggtc attttaggg  taaaaatgga tttagggaaa tttgatggca  2880
aatttgggtc aaaaaatggt gattttgggt caaaaaatga ttatttgg   tcatttag    2940
gagaaaaatg aatttaggga gatttgaggg caaatttggg tcgaaaaatg gtgattttgg  3000
gtgaaaaatg gacaatttg  ggtcatttta gggttaaaaa tgaatttagg gagattggac  3060
ggcaaatttg ggtcaaaaaa tggtgatttg gggtcaaaaa ataattattt tgggtcattt  3120
tagggataaa aaatgaattt agggagattt gaggcaaat  ttgggtcgaa aaatggtgat  3180
tttgggtgaa aaatggacaa ttttgggtca ttttagggat aaaaaatgaa tttagggcga  3240
tttgagccaa atttgggtca aaaatggtga ttttgggtga aaaattgaca gttttgggtc  3300
```

```
attttagggt taaaaatgaa tttagggaga ttggacggca aatttgggtc aaaaaatggt    3360
gatttggggt caaaaaatga ttattttggg tcattttagg gataaaaaat gaatttaggg    3420
agatgtgagg gcaaatttgg gtcgaaaaat ggtgattttg ggtgaaaaat tgacagtttt    3480
gggtcatttt agggatataa atggacttag agagatttga gggcaaattt gggtgaaaaa    3540
atggacaatt tgggtcattt ttgggatata aatgaatttta agatttgacg gcaaatttgg    3600
gtcaaaaaat ggtgatttgg gtcaaaaatg gtgattttgg ttgaaaaacg gccattttgg    3660
gtcattttag ggataaaaat gaatttaggg agatttgagg gcaaatttgg gtgaaaaaag    3720
ggcgatttgg gggtcatttt agggagaaaa atgaatttag ggcgatttga gggcaaattt    3780
gggtgaaaaa agggagattt tggtcatttt agggataaaa atgaatttta gggagaactg    3840
agggcaaatt tggtcaaaaa atgacaatt tgggtcgttc tagggagaaa aatgaatttt    3900
gggcgatttg agggtaaatt tgggtcgaaa aatggtgatt tgggtcaaaa aatgattatt    3960
ttgggtcatt taagggagaa aagggattta gggagatttg agggcaaatt tgggtcgaaa    4020
aattgtgatt tggggtcaaa aaatgacaat tttgggtcat tttagggata taaatggact    4080
tagagcgatt tgagggcaaa tttggggtgaa aaaatgacaa tttgggtcat tttagggata    4140
taaatgaatt tagggcgatt tgagggcaaa tttggttcga aaatggtgat tttgggtcaa    4200
tttagggagg aaaatgaatt taaggcaatt tgaaggcaaa tttgggtgaa aaaatgacaa    4260 tttgggggtca ttttaaagat aaaatgaatt tagggctatt tgagggcaaa tttgggtcaa    4320
aaaatggtga tttgggggtca aaaaatatgg tgattttgag tcgttttagg ggggaaaatg    4380
aatttaggga gatttgaggg caaatttggg tcaaaaaatg gtgattttttg gtcgttttag    4440 tgataaaaaa tgaatttagg gcagtttgag ggcaaatctg ggtcaaaaaa gggtgattttt    4500 gagtcaaaaa tagtgatttt gggtcatttt agggatataa atgaattcag ggagatttga    4560
gggcaaattt gagtcaaaaa tagtgatatg ggtcaaaagt ggtgattttg gttgaaaaac    4620
agtcattttg ggtcatttta gggattaaaa tgaacttagg gagatttgag ggcaaatttg    4680
ggtcaaaaaa tgacaatttt gggtcacttt acgaattaaa atgaattcag ggagatttga    4740
gggcaaattt gggtcaaaaa aatggtgatt tgggtcattt ttagggttaa aaatgaattc    4800
aggatgattt gaaggcaact ttgggtcaaa aaatgattaa tttgggtcat tttaaagagg    4860
aaaatgaatt tagggagatt tgagggcaaa ttcgggtgaa aattggacaa ttttgggtca    4920
ttttagggat aaaaatgaat ttagggagat ttgagggcaa atttgggtca aaaaatggtg    4980
attttgggtc gttttaggaa taaaaatgaa tttagggaga tttgagggca atttgggtc    5040 aaaaaatggt gatttggggt cattttcaga aggaaaatga ttattttccc cactaaaaat    5100
gtatattttg gggccaaatg gtgaaaaatg gtgattttta atcaaacgtc cccaaaattg    5160
gggaaatttc atcgatttga cccaaaattg agttttttt ccctgttaaa aatgtacatt    5220
ttggggtcaa tcgttgaaat gttcccattt ttcacttctt tgcccccaaa ttttgctttc    5280
cggtgagaaa ttacagtgtt aattaattaa taatcggtaa ttgagcgaca attaataatt    5340
attaattaat taataggtcc ttttttggtg actccttcgc ttttgggggcc aaaagtccat    5400 aaattggccc caaaaaatta atactgagta attggattcc aaagtattaa tgataaacat    5460
taaaagtgtt taattaatca tgatattaaa cataatttcg tttttattat cgatttatca    5520
acaacgatga acgataatac tttacaacaa tcgttaataa ttaattaatt aattaattaa    5580
ttaattaatt tctaataatt aattcgcatt atcggacacg agatgttgta atgattaata    5640
ataatttaat tcctaataat tagaagattc gttgaaaatt atctttacaa ataatcactt    5700
```

```
ctaataataa tgattaataa tagttaataa caataacaat aatgataata atattaataa      5760
tatgtgatat atttaatata aaattcgtat taatatatta tatctacaaa atatgatata      5820
aaatataata ttttatttat ataacacaca atttattatc attattatca ttattaatat      5880
catcattatt aatgttatcg aaatacttat ttagaaataa taaaaacgga tttaataatg      5940
gcaacaaaaa tattttatta atgttaaaaa aaaataatta ataatttcca aagattcgaa      6000
ttcggggcaa cgaacggcac tcgataattt ttaattaatt aatagtttga attaatcggt      6060 acttttaat cctccatttt gcccgaaatc gccgtttttt gccccaaatt ccccaccgcg       6120
gcgttaaaaa cataaagaaa ttaagcttca aaagtgccct tttttggggt tgtttttgacc     6180 ccccaaaaaa aatggccgaa ttgggggcgg ccgttttacg gttgggttca ttttgggttc     6240
aaaacagcca aaaatgggaa ctttgggttt cgaaaacaac aacaacaaaa aaacgggttt     6300
attttgggct cattttgggt gttttgggt caggaggaga aaaaatagga agtttgagag      6360
cgaaacaacg gccgcttttg gggggaaaac ggccctttt ggtcaacggc ggggaaaaa       6420 aaaaagcgga gttttgggg tgaaaagag cggtttggg taaatttggg ttttggggta       6480 aaagtgagg atttggggcg atgggagtta aaaaatgggt gttttatgg gggttcggtg      6540 cagttttcc tgtttgatgg ggggtttatt aatccggggg ggggaattaa tgagaattaa       6600
taatgttaat agaaatatct gggaaattaa tagcaattat taattgttaa tagttattaa     6660
tagttctata tatctcacat ctacgataca atataatatc gttataatca tatagtcgat     6720
atattacata taattatcag taataataat aagtaacaat aattagcagt aattaataat     6780
aataattaat agtattcgtt aataagatta ttgataataa ttaagtagta gtgattaata     6840
gagatgggat ttcgtgagaa atggaccaaa tttgggccgt tttgacccaa atttttggtg     6900 ggttttttt ccgattcttt gtgaatttcg ggtcggattc atcagcaatt aattacggtt      6960
attaggggct attagaggct tttaattggg attattagag acttttaagc ggatttgggg     7020
acttttaagt ggattttatg atttttttaag tggattttgg gtggatttta ccgcttttgg    7080 cgaatttttaa tggggattat tagaagttat tagtggttat tagaagtaat tagaagccgt   7140
taggaatgat tagaaatgat tagaaattat tagaaatgat tagaaataat gagaaataat    7200
tagaaataat gagaaataat gagaaataat tagaaaaatg agaaataatg agaaataatg    7260
agaaataatt agaaaatga gaaataagag gaatattaag tgaacatttt gtgattaatt      7320
acaaataatt gggaaatgag tagaaattat tagaaaatat tagaaataat cagaaaatta    7380
agtgaacatt ttgcgattaa ttagtgataa ttgggaaata attagaaata cttagaaata    7440
attaggaata agagaaatta ttagaaataa tacaaataat cagaaaataa tacaaataat    7500
tggaaataat cggaaataat cggaaataaa ttgaaataat gggaaacgat ggggaaatat     7560
tagaagcaat taagaaatta attgataaat tggaaataat gaggaattgt cagaaattaa    7620
tggaaataat ggggaaataa ttagaaatat tagaaataat cggaaaatta atgcaaaatag   7680 ttggtaataa cgagaaataa ggggaaaata atggaaataa tggaaaaata ttagaagcaa    7740
ttaagaaatt aattgataaa ttagaaacgt tgataaacaa tcggaaaata attgaaatgg    7800
aaataaatta gaaataattg gaaataatgg ggaaataatt agaaatatta gaaataatgg    7860
gaaatgatta agaaatatga gaaataatta gaaataatta gaaatattag aattaattaa    7920
tgggaaataa tggaaataa tggcaaaata ttagaaataa cgggaaatga ttaagaaata     7980
atcagaaata attagaaata ttagaaataa ttaatgggaa ataatgggaa ataatggcaa    8040
aatattagaa ataatgggaa atgattaaga aatatgagaa ataattagaa ataattagaa    8100
```

```
atattagaaa taatgggaa ataacggaaa tagtgggaaa taatgggaaa atattagaaa      8160
taatgggaaa taattaagaa atattagaaa taattagaaa tattagaatt aattaacggg      8220
gaaataacgg aaataattgc aattattgga attatcgggg aaataattgg attaaaaaaa      8280
aattaattgg gggtccgtgg gagtaattaa ggatcgatcg atactgaatg atgagaaata      8340
attagcatta attaattaat tagttgatta attaaggggg acagatatta agaaatcaat      8400
cggggtttta taacagcaga aaacggaccg aaatgaccca aaaatgaccc ccccaaaaaa      8460
gattcctaat taagatccgg actcattaag cctcattatc ccctgataa ttagcactaa        8520 ttaacggggt tcattaatta gccccaatag cccgaatcgc cgcttttta ttaataattc        8580 gtaatttttt tggcccaatt tgggcctttt ccgaacggca ctttgggact cgttaagaaa      8640
tgagggcctt aatgagctta attagcggcg ctaattaagg cggttaatga aggtcaatga      8700
agggagggct gaggggaaat ggggccaata tggaccagta gggaccagta tggaccagta      8760
tagaccagta tggaccagta tggggttact gggaccagta cggaccagta tggatttacc      8820
ggaaccagta tagaccagta tagaccagta tggaccagta tggaccagta tgggtgcact      8880
gggaccagta tagaccagta tggaccagta tggaccagta tgggtgcact gggaccagta      8940
cagaccagta tggatttacc ggaaccagta tagaccagta tagaccagta tggaccagta      9000
tggggttact gggaccagta tagaccagta tagaccagta tagaccagta tggagcagta      9060 tgggggtca cctggagctg tactggtgcc ggtaccagta tgaaccagta tggactagta        9120
tgggtgcact ggaaccagta tagaccagta tggaccagta tggggaggtc gccgggagct      9180
gtactggttc ttactggtgc taggaccagt acgaccagt atggaccagt atagaccagt        9240
atgggtgcca atatggacca gtatggggtt gccgggagct gtactggttt gtactggtgc      9300
ctgtaccagt atagaccagt acggaccagt atggaccagt acgggaggg tgccgggagc        9360 tgtactggcg ccggtaccag tatggaccag tatagaccag tatgggtgca ctgggaccag      9420
tatagaccag tatggaccag tatggggaag tgccgggagc tgtactggtg ctggtcccag      9480
tatggaccag tatggaccag tatggaccag taaggaccag tacgggttcc agtatggacc      9540
agtacggacc agtatggggg ggtgccgggt gctgtactgg tttgtactgg tgctggtgcc      9600
agtatagacc agtacggacc agtatggacc agtatggggg gtcacctgga gctgtactgg      9660
caccggtacc agtatggacc agtatggacc agtatgggtg cactgggacc agtacggacc      9720
agtacggggc gggggt                                                       9736

<210> SEQ ID NO 16
<211> LENGTH: 18396
<212> TYPE: DNA
<213> ORGANISM: artificial sequence
<220> FEATURE:
<223> OTHER INFORMATION: Synthetic vector construct

<400> SEQUENCE: 16
ctaaattgta agcgttaata ttttgttaaa attcgcgtta aattttttgtt aaatcagctc        60 attttttaac caataggccg aaatcggcaa aatcccttat aaatcaaaag aatagaccga      120
gatagggttg agtgttgttc cagtttggaa caagagtcca ctattaaaga acgtggactc      180
caacgtcaaa gggcgaaaaa ccgtctatca gggcgatggc ccactacgtg aaccatcacc      240
ctaatcaagt ttttggggt cgaggtgccg taaagcacta atcggaacc ctaaagggag         300 cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
```

```
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
cgcgcctggg aaatttggcc ctcttggccc aattttgccc aaaaatggca aatttgggg     720 tcatttcttc ccccgtaggt gagagcttca acctccagca gctccacgac tccaaaaaag    780
agacattttg cccatttctt gccattttt gacccaaatt ttggggtctt ttccccttcc     840
acggccactt tgaaacccta caaattactg cctctttttt tctccgtttt ttgcccccaaa   900 tctgcctttt tttcccccct ttttggggcc ctccgggagg aaacgtctcc accggtggcc    960
gctcaagtgg tgaacccaca aactttgggg taaaaacaca ggattttggt caacgttgta   1020
tcactgtggg ttgtagtgct tacggttgtg gtgcttatca cggtgctcca tcccataaca   1080 aaaccatcc tcattttggg gcaactttgg ccctttttgg tcaattttg ccccccacgt     1140 acgacgattt cccctcttc tttggccacc attgacccaa atttggggt tatttttcccc    1200 cttttacca atattaccaa aaaaaaatca attttttccca tcttccccag accacaaaat   1260
tgggattttt ttttggcctt tttcggctat ttttttgcccc aaaatccaac gattcccctc   1320
tcctcctcac ctccaaaaat ggggccattt tgtcccttt ccccattttc caccccctt     1380 cccccccctc tccacattta cagttttggg acgctcccaa tcttgccccg ttttgccca    1440 aaatcccct ctttccaggc attcgatccc aaaattgaga tatttgatca ttttaaccaa    1500
ttttccccca aaataccgcc tcctcactga cggccgcgt gccaaaaacg gggaattttc    1560
tcccaaatac gttcaatgtt ttccttttt ttgcccgttt ttgaccggtt ttgcccattt    1620
ttgtgcgttt ttaaccattt tttttacat ttttaaccaa aatttgtgtg ttttttacctt   1680 aagattcagc tcccatgggt gaaaaatgag aggtttctcc ccattcaaat tctacgactt   1740
ttgggatatc cctacgtgga gaatttgggg taaaaatgcc acaaatcggt taaaaatggc    1800
attttttggc taaaaaatgg catttttttgt tctgaaaata gcattttttg gctaaaattg    1860
ggggttttag ccctaaaata gggaggaaaa caatgaggat ttgaaacact ccgtcccccaa   1920 aattgaaatc tttgattctg gcatcattgg gtgatccgaa gtgaggaatt tggggtaaaa   1980
atggctcaaa ttggttaaaa ataaccgttt ttggtctgaa aatggcattt ttttggctaa   2040
aattggggtt tttagcccta aaatagggag gaaaacagtg aggatttgaa aactctgaac   2100
ccataaagtg aaatcctcaa ttttgggcat cattgggtga tcttaaggga ggaatttggg   2160
gcaaaaatgg ccaaattggt taagaatagc agttttttggt ctaaaaatgg cattttttgg   2220
ctaaaattgg ggttttttagc cctaaaatgg ggaggaatcc aatgaggatt tgaaacactc   2280
cgagcccaga attgaaatct tcgattttgg tcatctttgg gtgattctaa cggaggaatt   2340
tggggtaaaa acagcccaaa ttggttaaaa atggcagttt ttggtctaaa aatggcagtt   2400
tttgttctga aaatggcatt ttttggctaa aattggggtt tttgcccta aaatagtgag    2460 gaaaacaaca aggatttgaa aaacctgaag gcaaacaatg aaatcttcga ttttgggcca   2520
atattgcagg aatttggagc gaaggatggc caaaaacgg ttgtttttt ctttttaac      2580 caaaatgggc ggttttcgcc ccgagctagc ataacttcgt atagcataca ttatacgaag   2640
ttataagcgt aatctggaac atcgtatgta ccggatccga agcaggcttt cctggaaggt   2700
cctgaagggg ggcgtccgcg ggagctcacg gggacagccc ccccccaaag ccccccaggga  2760 tgtaattacg tccctccccc gctaggggc agcagcgagc cgcccggggc tccgctccgg   2820
```

```
tccggcgctc cccccgcatc cccgagccgg cagcgtgcgg ggacagcccg ggcacgggga      2880
aggtggcacg ggatcgcttt cctctgaacg cttctcgctg ctctttgagc ctgcagacac      2940 ctgggggat acgggaaaa agctttaggc tgagaagcag gctttcctgg aaggtcctgg        3000 aaggggggcgt ccgcgggagc tcacggggac agccccccc caaagccccc agggatgtaa     3060
ttacgtccct ccccgctag ggggcagcag cgagccgccc ggggctccgc tccggtccgg       3120
cgctcccccc gcatcccga gccggcagcg tgcggggaca gcccgggcac ggggaaggtg      3180
gcacgggatc gctttcctct gaacgcttct cgctgctctt tgagcctgca gacacctggg      3240
gggatacggg gaaaaagctt taggctgaac tagctagtct cgaggtcgag gtgagcccca     3300
cgttctgctt cactctcccc atctccccc cctccccacc cccaattttg tatttattta       3360 tttttaatt attttgtgca gcgatggggg cgggggggg gggggcgcgc gccaggcggg        3420
gcggggcggg gcgaggggcg gggcggggcg aggcggagag gtgcggcggc agccaatcag     3480
agcggcgcgc tccgaaagtt ccttttatg gcgaggcggc ggcggcggcg gccctataaa      3540
aagcgaagcg cgcggcgggc gggagtcgct gcgttgcctt cgcccgtgc cccgctccgc       3600 gccgcctcgc gccgcccgcc ccggctctga ctgaccgcgt tactcccaca ggtgagcggg      3660
cgggacggcc cttctcctcc gggctgtaat tagcgcttgg tttaatgacg gctcgtttct      3720
tttctgtggc tgcgtgaaag ccttaaaggg ctccgggagg gccctttgtg cgggggggag     3780
cggctcgggg ggtgcgtgcg tgtgtgtgtg cgtggggagc gccgcgtgcg gcccgcgctg     3840
cccggcggct gtgagcgctg cgggcgcggc gcgggctttt gtgcgctccg cgtgtgcgcg     3900
aggggagcgc ggccgggggc ggtgccccgc ggtgcgggg ggctgcgagg ggaacaaagg      3960
ctgcgtgcgg ggtgtgtgcg tgggggggtg agcaggggggt gtgggcgcgg cggtcgggct   4020
gtaacccccc cctgcacccc cctccccgag ttgctgagca cggcccggct tcgggtgcgg    4080
ggctccgtgc ggggcgtggc gcggggctcg ccgtgccggg cggggggtgg cggcaggtgg    4140
gggtgccggg cggggcgggg ccgcctcggg ccggggaggg ctcggggag gggcgcggcg     4200 gccccggagc gccggcggct gtcgaggcgc ggcgagccgc agccattgcc tttttatggta   4260 atcgtgcgag agggcgcagg gacttccttt gtcccaaatc tggcggagcc gaaatctggg    4320
aggcgccgcc gcacccccctc tagcggggcgc gggcgaagcg gtgcggcgcc ggcaggaagg   4380
aaatgggcgg ggagggccctt cgtgcgtcgc gcgccgccg tccccttctc catctccagc    4440
ctcggggctg ccgcagggggg acggctgcct tcggggggga cggggcaggg cggggttcgg   4500
cttctggcgt gtgaccggcg gctctagagc ctctgctaac catgttcatg ccttcttctt    4560
tttcctacag ctcctgggca acgtgctggt tgttgtgctg tctcatcatt ttggcaaaga    4620
attatcgcat gcctgcgtcg acggtaccgc gggcccggga tccaccggtc gccaccatgg    4680
tgagcaaggg cgaggagctg ttcaccgggg tggtgcccat cctggtcgag ctggacggcg    4740
acgtaaacgg ccacaagttc agcgtgtccg gcgaggcga gggcgatgcc acctacggca    4800
agctgaccct gaagttcatc tgcaccaccg gcaagctgcc cgtgccctgg cccaccctcg   4860
tgaccaccct gacctacggc gtgcagtgct tcagccgcta ccccgaccac atgaagcagc    4920
acgacttctt caagtccgcc atgcccgaag gctacgtcca ggagcgcacc atcttcttca    4980
aggacgacgg caactacaag acccgcgccg aggtgaagtt cgagggcgac accctggtga   5040
accgcatcga gctgaagggc atcgacttca aggaggacgg caacatcctg gggcacaagc   5100
tggagtacaa ctacaacagc cacaacgtct atatcatggc cgacaagcag aagaacggca   5160
tcaaggtgaa cttcaagatc cgccacaaca tcgaggacgg cagcgtgcag ctcgccgacc   5220
```

```
actaccagca gaacacccce atcggcgacg gcccegtget getgecegac aaccactace      5280 tgagcaccea gtecgecetg agcaaagace ccaacgagaa gegegateac atggtcetge      5340 tggagttcgt gaccgccgcc gggatcactc tcggcatgga cgagctgtac aagtaaagcg      5400
gccggccgcg actctagatc ataatcagcc ataccacatt tgtagaggtt ttacttgctt      5460
taaaaaacct cccacacctc ccctgaacc tgaaacataa aatgaatgca attgttgttg       5520
ttaacttgtt tattgcagct tataatggtt acaaataaag caatagcatc acaaatttca      5580
caaataaagc attttttca ctgcattcta gttgtggttt gtccaaactc atcaatgtat       5640
cttaaggaac cccttcctcg acattgatta ttgactagct agttattaat agtaatcaat      5700
tacggggtca ttagttcata gcccatatat ggagttccgc gttacataac ttacggtaaa     5760
tggcccgcct ggctgaccgc ccaacgaccc ccgcccattg acgtcaataa tgacgtatgt     5820
tcccatagta acgccaatag ggactttcca ttgacgtcaa tgggtggact atttacggta     5880
aactgcccac ttggcagtac atcaagtgta tcatatgcca agtacgcccc ctattgacgt     5940
caatgacggt aaatggcccg cctggcatta tgcccagtac atgaccttat ggactttcc      6000 tacttggcag tacatctacg tattagtcat cgctattacc atgggtcgag gtgagcccca      6060
cgttctgctt cactctcccc atctcccccc cctccccacc cccaattttg tatttattta      6120
ttttttaatt attttgtgca gcgatggggg cggggggggg ggggcgcgc gccaggcggg       6180 gcggggcggg gcgaggggcg gggcggggcg aggcggagag gtgcggcggc agccaatcag      6240
agcggcgcgc tccgaaagtt cctttttatg gcgaggcggc ggcggcggcg ccctataaa      6300 aagcgaagcg cgcggcgggc gggagtcgct gcgttgcctt cgccccgtgc ccgctccgc      6360 gccgcctcgc gccgcccgcc ccggctctga ctgaccgcgt tactcccaca ggtgagcggg     6420
cgggacggcc cttctcctcc gggctgtaat tagcgcttgg tttaatgacg gctcgtttct    6480
tttctgtggc tgcgtgaaag ccttaaaggg ctccggagg gccctttgtg cggggggag      6540 cggctcgggg ggtgcgtgcg tgtgtgtgtg cgtggggagc gccgcgtgcg gcccgcgctg    6600
cccggcggct gtgagcgctg cgggcgcggc gcggggcttt gtgcgctccg cgtgtgcgcg    6660
aggggagcgc ggccggggc ggtgcccgc ggtgcggggg ggctgcgagg ggaacaaagg      6720
ctgcgtgcgg ggtgtgtgcg tgggggggtg agcaggggt gtgggcgcgg cggtcgggct    6780 gtaaccccc cctgcacccc cctccccgag ttgctgagca cggccccggct tcgggtgcgg     6840 ggctccgtgc ggggcgtggc gcggggctcg ccgtgccggg cggggggtgg cggcaggtgg    6900
gggtgccggg cggggcgggg ccgcctcggg ccggggaggg ctcggggag gggcgcggcg      6960 gccccggagc gccggcggct gtcgaggcgc ggcgagccgc agccattgcc ttttatggta     7020
atcgtgcgag agggcgcagg gacttccttt gtcccaaatc tggcggagcc gaaatctggg     7080
aggcgccgcc gcaccccctc tagcgggcgc gggcgaagcg gtgcggcgcc ggcaggaagg    7140
aaatgggcgg ggagggcctt cgtgcgtcgc cgcgccgccg tcccttctc catctccagc      7200 ctcggggctg ccgcagggg acggctgcct tcggggggga cggggcaggg cggggttcgg     7260
cttctggcgt gtgaccggcg gctctagagc ctctgctaac catgttcatg ccttcttctt     7320
tttcctacag ctcctgggca acgtgctggt tattgtgctg tctcatcatt ttggcaaaga     7380
attcctagcg ccaccatgac cgagtacaag cctaccgtgc gcctggccac tcgcgatgat      7440 gtgcccgcg ccgtccgcac tctgccgcc gctttcgccg actacccgc tacccggcac      7500 accgtggacc ccgaccggca catcgagcgt gtgacagagt gcaggagct gttcctgacc     7560 cgcgtcgggc tggacatcgg caaggtgtgg gtagccgacg acggcgcggc cgtggccgtg    7620
```

```
tggactaccc ccgagagcgt tgaggccggc gccgtgttcg ccgagatcgg cccccgaatg   7680
gccgagctga gcggcagccg cctggccgcc cagcagcaaa tggagggcct gcttgccccc   7740
catcgtccca aggagcctgc ctggtttctg gccactgtag gagtgagccc cgaccaccag   7800
ggcaagggct tgggcagcgc cgtcgtgttg cccggcgtag aggccgccga acgcgccggt   7860
gtgcccgcct ttctcgaaac aagcgcacca agaaaccttc cattctacga gcgcctgggc   7920
ttcaccgtga ccgccgatgt cgaggtgccc gagggaccta ggacctggtg tatgacacga   7980
aaacctggcg cctaatgatc tagaaccggt catggccgca ataaaatatc tttatttca    8040 ttacatctgt gtgttggttt tttgtgtgtt cgaacctgca gcccggggga tccgaagcag   8100
gctttcctgg aaggtcctgg aagggggcgt ccgcgggagc tcacggggac agcccccccc   8160
caaagccccc agggatgtaa ttacgtccct ccccgctag ggggcagcag cgagccgccc    8220
ggggctccgc tccggtccgg cgctcccccc gcatccccga gccggcagcg tgcggggaca   8280
gcccgggcac ggggaaggtg gcacgggatc gctttcctct gaacgcttct cgctgctctt   8340
tgagcctgca gacacctggg gggatacggg gaaaaagctt taggctgaga agcaggcttt   8400
cctggaaggt cctggaaggg ggcgtccgcg ggagctcacg ggacagccc ccccccaaag    8460 cccccaggga tgtaattacg tccctccccc gctaggggc agcagcgagc cgcccggggc    8520
tccgctccgg tccggcgctc ccccgcatc cccgagccgg cagcgtgcgg ggacagcccg    8580
ggcacgggga aggtggcacg ggatcgcttt cctctgaacg cttctcgctg ctctttgagc   8640
ctgcagacac ctgggggat acggggaaaa agctttaggc tgaactagaa tgcatataac    8700
ttcgtatagc atacattata cgaagttatg atcccccaa atcaatctaa agtatatatg    8760
agtaacctga ggctatggca gggcctgccg ccccgacgtt ggctgcgagc cctgggcctt   8820
cacccgaact tggggggtgg ggtgggaaa aggaagaaac gcgggcgtat tggcccaat     8880 ggggtctcgg tggggtatcg acagagtgcc agccctggga ccgaaccccg cgtttatgaa   8940
caaacgaccc aacaccgtgc gttttattct gtctttttat tgccgtcata gcgcgggttc   9000
cttccggtat tgtctccttc cgtgtttcag ttagcctccc cctagggtgg gcgaagaact   9060
ccagcatgag atccccgcgc tggaggatca tccagccggc gtcccggaaa acgattccga   9120
agcccaacct ttcatagaag gcggcggtgg aatcgaaatc tcgtgatggc aggttgggcg   9180
tcgcttggtc ggtcatttcg aaccccagag tcccgctcag aagaactcgt caagaaggcg   9240
atagaaggcg atgcgctgcg aatcgggagc ggcgataccg taaagcacga ggaagcggtc   9300
agcccattcg ccgccaagct cttcagcaat atcacgggta gccaacgcta tgtcctgata   9360
gcggtccgcc acacccagcc ggccacagtc gatgaatcca gaaaagcggc cattttccac   9420
catgatattc ggcaagcagg catcgccatg ggtcacgacg agatcctcgc cgtcgggcat   9480
gctcgccttg agcctggcga acagttcggc tggcgcgagc cctgatgct cttcgtccag    9540 atcatcctga tcgacaagac cggcttccat ccgagtacgt gctcgctcga tgcgatgttt   9600
cgcttggtgg tcgaatgggc aggtagccgg atcaagcgta tgcagccgcc gcattgcatc   9660
agccatgatg gatactttct cggcaggagc aaggtgagat gacaggagat cctgccccgg   9720
cacttcgccc aatagcagcc agtcccttcc cgcttcagtg acaacgtcga gcacagctgc   9780
gcaaggaacg cccgtcgtgg ccagccacga tagccgcgct gcctcgtctt gcagttcatt   9840
cagggcaccg gacaggtcgg tcttgacaaa aagaaccggg cgcccctgcg ctgacagccg   9900
gaacacggcg gcatcagagc agccgattgt ctgttgtgcc cagtcatagc cgaatagcct   9960
ctccacccaa gcggccggag aacctgcgtg caatccatct tgttcaatca tgcgaaacga  10020
```

```
tcctcatcct gtctcttgat cgattacgcc cccaactgag agaactcaaa ggttacccca    10080 gttgggggcac actagtggcg gtctgagggg aaaatgtcgt tttggggcca ttttgggcca    10140
tttgagggga aatttgggtc aaaaaatgac gattttgggt cattttaggg ataaaaaatg    10200
aatttaggga gatttgaggg caaatttggg tcaaaaaatg gtgatttggg gtcaaaaatg    10260
gacaattttg ggtcatttta gggttaaaaa tggatttagg gaaatttgat ggcaaatttg    10320
ggtcaaaaaa tggtgatttt gggtcaaaaa atgattattt tgggtcattt tagggagaaa    10380
aatgaattta gggagatttg aggcaaatt tgggtcgaaa aatggtgatt ttgggtgaaa    10440
aatggacaat tttgggtcat tttagggtta aaaatgaatt tagggagatt ggacggcaaa    10500
tttgggtcaa aaaatggtga tttggggtca aaaataatt attttgggtc attttaggga    10560
taaaaaatga atttagggag atttgagggc aaatttgggt cgaaaatgg tgattttggg    10620 tgaaaaatgg acaattttgg gtcattttag ggataaaaaa tgaatttagg gcgatttgag    10680
ccaaatttgg gtcaaaaatg gtgatttggg gtgaaaaatt gacagtttttg ggtcatttta    10740 gggttaaaaa tgaatttagg gagattggac ggcaaatttg ggtcaaaaaa tggtgatttg    10800
gggtcaaaaa atgattattt tgggtcattt tagggataaa aaatgaattt agggagatgt    10860
gagggcaaat ttgggtcgaa aaatggtgat tttgggtgaa aaattgacag ttttgggtca    10920
ttttagggat ataaatgaac ttagagagat tgagggcaa atttgggtga aaaatggac    10980 aatttggggtc atttttggga tataaatgaa tttaagattt gacggcaaat ttgggtcaaa    11040
aaatggtgat ttgggtcaaa aatggtgatt ttggttgaaa aacggccatt ttgggtcatt    11100
ttagggataa aaatgaattt agggagattt gagggcaaat ttgggtgaaa aagggcgat    11160 ttgggggtca ttttagggag aaaatgaat ttagggcgat tgagggcaa atttgggtga    11220 aaaagggag attttggtc atttttaggga taaaaatgaa tttagggaga actgagggca    11280
aatttgggtc aaaaaatgac aatttgggtc gttctaggga gaaaaatgaa ttttgggcga    11340
tttgagggta aatttgggtc gaaaatggt gatttgggtc aaaaatgat tattttgggt    11400 cattttaaggg agaaaaggga tttaggggaga tttgagggca aatttgggtc gaaaaattgt    11460
gatttggggt caaaaaatga caattttggg tcattttagg gatataaatg gacttagagc    11520
gatttgaggg caaatttggg tgaaaaaatg acaatttggg tcattttagg gatataaatg    11580
aatttagggc gatttgaggg caaatttggt tcgaaaatgg tgattttggg tcaatttagg    11640
gaggaaaatg aatttaaggc aatttgaagg caaatttggg tgaaaaaatg acaatttggg    11700
gtcattttaa agataaaatg aatttagggc tatttgaggg caaatttggg tcaaaaaatg    11760
gtgatttggg gtcaaaaaat atggtgattt tgagtcgttt taggggggaa aatgaattta    11820
gggagatttg agggcaaatt tgggtcaaaa aatggtgatt tttggtcgtt ttagtgataa    11880
aaaatgaatt tagggcagtt tgagggcaaa tctgggtcaa aaagggtga ttttgagtca    11940 aaaatagtga ttttgggtca ttttagggat ataaatgaat tcaggagat ttgagggcaa    12000 atttgagtca aaaatagtga tatgggtcaa aagtggtgat tttggttgaa aaacagtcat    12060
tttgggtcat tttagggatt aaaatgaact tagggagat ttgagggcaaa tttgggtcaa    12120 aaaatgacaa tttggggtca ctttacgaat taaaatgaat tcaggagat ttgagggcaa    12180 atttggggtca aaaaaatggt gattttgggt cattttaggg ttaaaaatga attcaggatg    12240
atttgaaggc aacttgggt caaaaaaatg attatttggg tcattttaaa gaggaaaatg    12300
aatttagggg atttgaggg caaattcggg tgaaaattgg acaattttgg gtcattttag    12360
ggataaaaat gaatttaggg agatttgagg gcaaatttgg gtcaaaaaat ggtgattttg    12420
```

```
ggtcgtttta ggaataaaaa tgaatttagg gagatttgag ggcaaatttg ggtcaaaaaa    12480
tggtgatttg gggtcatttt cagaaggaaa atgattattt tccccactaa aaatgtatat    12540
tttgggccca aatggtgaaa aatggtgatt tttaatcaaa cgtccccaaa attggggaaa    12600
tttcatcgat ttgacccaaa attgagtttt ttttccctgt taaaaatgta cattttgggg    12660
tcaatcgttg aaatgttccc attttttcact tctttgcccc caaattttgc tttccggtga    12720
gaaattacag tgttaattaa ttaataatcg gtaattgagc gacaattaat aattattaat    12780
taattaatag gtccttttttt ggtgactcct tcgcttttgg ggccaaaagt ccataaattg    12840
gccccaaaaa attaatactg agtaattgga ttccaaagta ttaatgataa acattaaaag    12900
tgtttaatta atcatgatat taaacataat ttcgttttta ttatcgatttt atcaacaacg    12960 atgaacgata atactttaca acaatcgtta ataattaatt aattaattaa ttaattaatt    13020
aatttctaat aattaattcg cattatcgga cacgagatgt tgtaatgatt aataataatt    13080
taattcctaa taattagaag attcgttgaa aattatcttt acaaataatc acttctaata    13140
ataatgatta ataatagtta ataacaataa caataatgat aataatatta ataatatgtg    13200
atatatttaa tataaaaattc gtattaatat attatatcta caaaatatga tataaaatat    13260
aatattttat ttatatataa cacaatttat tatcattatt atcattatta atatcatcat    13320
tattaatgtt atcgaaatac ttatttagaa ataataaaaa cggatttaat aatggcaaca    13380
aaaatatttt attaatgtta aaaaaaaata attaataatt tccaaagatt cgaattcggg    13440
gcaacgaacg gcactcgata atttttaatt aattaatagt ttgaattaat cggtactttt    13500
taatcctcca ttttgcccga aatcgccgtt ttttgcccca aattcccac cgcggcgtta    13560 aaaacataaa gaaattaagc ttcaaaagtg ccctttttg gggttgtttt gaccccccaa    13620
aaaaaatggc cgaattgggg gcggccgttt tacggttggg ttcattttgg gttcaaaaca    13680
gccaaaaatg ggaacttggg gtttcgaaaa caacaacaac aaaaaaacgg gtttatttg    13740 ggctcatttt gggtgttttt gggtcaggag gagaaaaaat aggaagtttg agagcgaaac    13800
aacggccgct tttggggga aaacggccct ttttggtcaa cggcggggga aaaaaaaag    13860 cggagttttt ggggtgaaaa agagcggttt tgggtaaatt tgggttttgg ggtaaaagtg    13920
gaggatttgg ggcgatggga gttaaaaaat gggtgttttt atggggttc ggtgcagttt    13980 ttcctgtttg atggggggtt tattaatccg ggggggggaa ttaatgagaa ttaataatgt    14040
taatagaaat atctgggaaa ttaatagcaa ttattaattg ttaatagtta ttaatagttc    14100
tatatatctc acatctacga tacaatataa tatcgttata atcatatagt cgatatatta    14160
catataatta tcagtaataa taataagtaa caataattag cagtaattaa taataataat    14220
taatagtatt cgttaataag attattgata ataattaagt agtagtgatt aatagagatg    14280
ggatttcgtg agaaatggac caaatttggg ccgttttgac ccaaattttt ggtgggtttt    14340
ttttccgatt ctttgtgaat ttcggtcgg attcatcagc aattaattac ggttattagg    14400
ggctattaga ggctttttaat tgggattatt agagactttt aagcggattt ggggactttt    14460
aagtggattt tatgattttt taagtggatt ttgggtggat tttaccgctt ttggcgaatt    14520
ttaatgggga ttattagaag ttattagtgg ttattagaag taattagaag ccgttaggaa    14580
tgattagaaa tgattagaaa ttattagaaa tgattagaaa taatgagaaa taattagaaa    14640
taatgagaaa taatgagaaa taattagaaa aatgagaaat aatgagaaat aatgagaaat    14700
aattagaaaa atgagaaata agaggaatat taagtgaaca ttttgtgatt aattacaaat    14760
aattgggaaa tgagtagaaa ttattagaaa atattagaaa taatcagaaa attaagtgaa    14820
```

```
cattttgcga ttaattagtg ataattggga aataattaga aatacttaga aataattagg   14880
aataagagaa attattagaa ataatacaaa taatcagaaa ataatacaaa taattggaaa   14940
taatcggaaa taatcggaaa ataattgaaa taatgggaaa cgatggggaa atattagaag   15000
caattaagaa attaattgat aaattggaaa taatgaggaa ttgtcagaaa ttaatggaaa   15060
taatggggaa ataattagaa atattagaaa taatcggaaa attaatgcaa atagttggta   15120
ataacgagaa ataaggggga aataatggaa ataatgggaa aatattagaa gcaattaaga   15180
aattaattga taaattagaa acgttgataa acaatcggaa aataattgaa atggaaataa   15240
attagaaata attggaaata atggggaaat aattagaaat attagaaata atgggaaatg   15300
attaagaaat atgagaaata attagaaata attagaaata ttagaattaa ttaatgggaa   15360
ataatgggaa ataatggcaa aatattagaa ataacgggaa atgattaaga aataatcaga   15420
aataattaga aatattagaa ataattaatg ggaaataatg ggaaataatg gcaaaatatt   15480
agaaataatg ggaaatgatt aagaaatatg agaaataatt agaaataatt agaaatatta   15540
gaaataatgg ggaaataacg gaaatagtgg gaaataatgg gaaatatatta gaaataatgg   15600 gaaataatta agaaatatta gaaataatta gaaatattag aattaattaa cggggaaata   15660
acggaaataa ttgcaattat tggaattatc ggggaaataa ttggattaaa aaaaaattaa   15720 ttggggggtcc gtgggagtaa ttaaggatcg atcgatactg aatgatgaga aataattagc   15780
attaattaat taattagttg attaattaag ggggacagat attaagaaat caatcggggt   15840
tttataacag cagaaaacgg accgaaatga cccaaaaatg accccccccaa aaaagattcc   15900 taattaagat ccggactcat taagcctcat tatccccctg ataattagca ctaattaacg   15960
gggttcatta attagccccca atagcccgaa tcgccgcttt ttaattaata attcgtaatt   16020
tttttggccc aatttgggcc ttttccgaac ggcactttgg gactcgttaa gaaatgaggg   16080
ccttaatgag cttaattagc ggcgctaatt aaggcggtta atgaaggtca atgaagggag   16140
ggctgagggg aaatggggcc aatatgcggc cgcggccgcc accgcggtgg agctccagct   16200
tttgttccct ttagtgaggg ttaattgcgc gcttggcgta atcatggtca tagctgtttc   16260
ctgtgtgaaa ttgttatccg ctcacaattc cacacaacat acgagccgga agcataaagt   16320
gtaaagcctg gggtgcctaa tgagtgagct aactcacatt aattgcgttg cgctcactgc   16380
ccgctttcca gtcgggaaac ctgtcgtgcc agctgcatta atgaatcggc caacgcgcgg   16440
ggagaggcgg tttgcgtatt gggcgctctt ccgcttcctc gctcactgac tcgctgcgct   16500
cggtcgttcg gctgcggcga gcggtatcag ctcactcaaa ggcggtaata cggttatcca   16560
cagaatcagg ggataacgca ggaaagaaca tgtgagcaaa aggccagcaa aaggccagga   16620
accgtaaaaa ggccgcgttg ctggcgtttt tccataggct ccgcccccct gacgagcatc   16680
acaaaaatcg acgctcaagt cagaggtggc gaaacccgac aggactataa agataccagg   16740
cgtttccccc tggaagctcc ctcgtgcgct ctcctgttcc gaccctgccg cttaccggat   16800
acctgtccgc ctttctccct tcgggaagcg tggcgctttc tcatagctca cgctgtaggt   16860
atctcagttc ggtgtaggtc gttcgctcca agctgggctg tgtgcacgaa ccccccgttc   16920
agcccgaccg ctgcgcctta tccggtaact atcgtcttga gtccaacccg gtaagacacg   16980
acttatcgcc actggcagca gccactggta acaggattag cagagcgagg tatgtaggcg   17040
gtgctacaga gttcttgaag tggtggccta actacggcta cactagaagg acagtatttg   17100
gtatctgcgc tctgctgaag ccagttacct tcggaaaaag agttggtagc tcttgatccg   17160
gcaaacaaac caccgctggt agcggtggtt ttttttgtttg caagcagcag attacgcgca   17220
```

-continued

```
gaaaaaaagg atctcaagaa gatcctttga tcttttctac ggggtctgac gctcagtgga   17280
acgaaaactc acgttaaggg attttggtca tgagattatc aaaaaggatc ttcacctaga   17340
tccttttaaa ttaaaaatga agttttaaat caatctaaag tatatatgag taaacttggt   17400
ctgacagtta ccaatgctta atcagtgagg cacctatctc agcgatctgt ctatttcgtt   17460
catccatagt tgcctgactc cccgtcgtgt agataactac gatacgggag ggcttaccat   17520
ctggccccag tgctgcaatg ataccgcgag acccacgctc accggctcca gatttatcag   17580
caataaacca gccagccgga agggccgagc gcagaagtgg tcctgcaact ttatccgcct   17640
ccatccagtc tattaattgt tgccgggaag ctagagtaag tagttcgcca gttaatagtt   17700
tgcgcaacgt tgttgccatt gctacaggca tcgtggtgtc acgctcgtcg tttggtatgg   17760
cttcattcag ctccggttcc caacgatcaa ggcgagttac atgatccccc atgttgtgca   17820
aaaaagcggt tagctccttc ggtcctccga tcgttgtcag aagtaagttg gccgcagtgt   17880
tatcactcat ggttatggca gcactgcata attctcttac tgtcatgcca tccgtaagat   17940
gcttttctgt gactggtgag tactcaacca agtcattctg agaatagtgt atgcggcgac   18000
cgagttgctc ttgcccggcg tcaatacggg ataataccgc gccacatagc agaactttaa   18060
aagtgctcat cattggaaaa cgttcttcgg ggcgaaaact ctcaaggatc ttaccgctgt   18120
tgagatccag ttcgatgtaa cccactcgtg cacccaactg atcttcagca tcttttactt   18180
tcaccagcgt ttctgggtga gcaaaaacag gaaggcaaaa tgccgcaaaa agggaataa   18240
gggcgacacg gaaatgttga atactcatac tcttcctttt tcaatattat tgaagcattt   18300
atcagggtta ttgtctcatg agcggataca tatttgaatg tatttagaaa aataaacaaa   18360
taggggttcc gcgcacattt ccccgaaaag tgccac                             18396
```

TRANSGENIC CHICKEN COMPRISING AN INACTIVATED IMMUNOGLOBULIN GENE

CROSS-REFERENCING

This application claims the benefit of U.S. provisional application Ser. No. 61/489,638, filed May 24, 2011, which application is incorporated by reference herein.

GOVERNMENT SUPPORT

This invention was made with Government support under Small Business Innovation Research contract R43 GM090626-01. The Government has certain rights in this invention.

BACKGROUND

During the past century, antibodies have been used therapeutically. Initially, therapeutic antibodies were administered as the naturally occurring polyclonal mixture from sera from immunized animals. While these products were efficacious, the serious side effects created by the anti-animal immune response of patients limited their use. Subsequently, monoclonal antibodies recovered from immunized mice were spliced onto a human constant region to produce chimeric antibodies that are approximately 70% human and 30% murine. The intensity of the anti-murine antibody response in patients treated with chimeric antibodies is significantly reduced. The ultimate goal of recovering fully human antibodies from immunized animals has been achieved by inactivating the endogenous immunoglobulin genes and substituting their human counterparts in the animal genome.

SUMMARY

Provided herein is a germline competent chicken cell comprising an endogenous heavy chain immunoglobulin locus in which at least a portion of the endogenous JH region is deleted. In particular embodiments, the JH region is replaced by a sequence that comprises a selectable marker. In some embodiments, the cell may be present in vitro. In other embodiments, the cell may be present in vivo. The cell may be a gonocyte or a primordial germ cell, for example.

Also provided herein is a chicken comprising an endogenous heavy chain immunoglobulin locus in which at least a portion of the endogenous JH region is deleted. In particular embodiments, the endogenous heavy chain immunoglobulin locus in which at least a portion of the endogenous JH region is deleted is in a germline cell of said chicken. In some cases, the chicken may be chimeric for cells that comprise said endogenous heavy chain immunoglobulin locus in which at least a portion of the endogenous JH region is deleted.

In particular embodiments, the chicken may be a transgenic chicken, and the chicken may be homozygous or heterozygous for the locus. The chicken may additionally contain an inactivated light chain locus.

In certain cases, any deleted portion of the genome may be replaced by another sequence.

Also provided are isolated nucleic acids. In one embodiment, the isolated sequence is at least 95% identical to nucleotides 1760 to 1957 of SEQ ID NO:15. In another embodiment, the isolated sequence may be at least 95% identical to nucleotides 2865-4932 of SEQ ID NO:15. In some embodiments, an isolated polynucleotide may comprise: the JH region of a chicken heavy chain immunoglobulin locus; and at least 400 bp of the sequence that flanks the 5' end of said JH region in said locus; and at least 400 bp of the sequence that flanks the 3' end of said JH region in said locus. In certain cases, the JH region may be at least 95% identical to nucleotides 2324-2380 of SEQ ID NO: 15.

A vector for inactivating the endogenous heavy chain immunoglobulin locus of a chicken genome is also provided. In certain cases, the vector may comprise: in order from 5' to 3': at least 400 bp 5' of the JH region of said heavy chain immunoglobulin locus; a selectable marker cassette; and at least 400 bp 3' of the JH region of said heavy chain immunoglobulin locus, wherein said vector does not contain said JH region. In certain cases, the vector contains the VH or C regions of said endogenous heavy chain immunoglobulin locus. In some cases, the at least 400 bp 5' of the JH region comprises a nucleotide sequence that is at least 95% identical to nucleotides 1760 to 1957 of SEQ ID NO:15. In some cases, the at least 400 bp 3' of the JH region comprises a nucleotide sequence that is at least 95% identical to nucleotides 2865-4932 of SEQ ID NO:15.

Also provided is a germline competent chicken cell comprising an endogenous light chain immunoglobulin locus in which the endogenous V-J-C region or a portion of the endogenous V-J region has been inactivated. In these embodiments, the V-J-C region may be replaced by a sequence that comprises a selectable marker. As above, the cell may be present in vitro or in vivo, and may be a gonocyte or a primordial germ cell, for example.

A chimeric chicken comprising an above-described cell in the germline of the chicken is also provided, as is a transgenic chicken comprising an endogenous light chain immunoglobulin locus in which the endogenous V-J-C region or a portion of the endogenous V-J-C has been inactivated. The chicken may be homozygous or heterozygous for said locus.

Also provided is a vector for inactivating the endogenous light chain immunoglobulin locus of a chicken genome, comprising, in order from 5' to 3': at least 400 bp 5' of the V region of said light chain immunoglobulin locus; a selectable marker cassette; and at least 400 bp 3' of the C region of said light chain immunoglobulin locus.

DEFINITIONS

Figure 1:
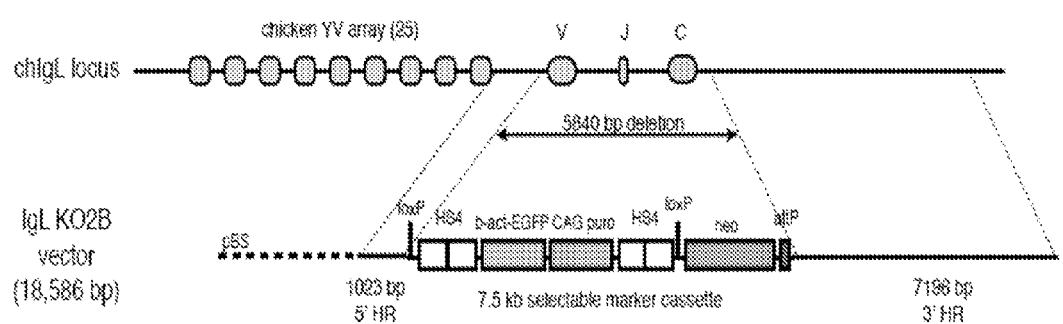
FIG. 1 schematically illustrates an IgL-VJC knockout vector.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "gene" refers to a nucleic acid sequence comprised of a promoter region, a coding sequence, and a 3'UTR.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

The term "progeny" or "off-spring" refers to any and all future generations derived and descending from a particular animal. Thus, progeny of any successive generation are included herein such that the progeny, the F1, F2, F3, generations and so on are included in this definition.

The phrase "transgenic chicken" refers to a chicken comprising cells containing foreign nucleic acid (i.e., recombinant nucleic acid that is not native to the animal). The foreign nucleic acid may be present in all cells of the animal or in some but not all cells of the animal. The foreign nucleic acid molecule is called a "transgene" and may contain one or many genes, cDNA, etc. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal. Alternatively, a transgenic animal may be produced by transfer of a nucleus from a genetically modified somatic cell or by transfer of a genetically modified pluripotential cell such as an embryonic stem cell or a primordial germ cell.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. In the context of gene conversion, two nucleic acids sequences are operably linked if one sequence can "donate" sequence to the other by gene conversion. If two sequences are unlinked in that one can donate sequence to the other via gene conversion, the donating sequences may be upstream or downstream of the other, and the two sequences may be proximal to each other, i.e., in that there are no other intervening genes. "Unlinked" means that the associated genetic elements are not closely associated with one another and the function of one does not affect the other.

The terms "upstream" and "downstream" are used with reference to the direction of transcription.

The term "homozygous" indicates that identical alleles reside at the same loci on homologous chromosomes. In contrast, "heterozygous" indicates that different alleles reside at the same loci on homologous chromosomes. A transgenic animal may be homozygous or heterozygous for a transgene.

The term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "replacing", in the context of replacing one genetic locus with another, refers to a single step protocol or multiple step protocol.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

As used herein the term "isolated," when used in the context of an isolated nucleic acid, refers to a nucleic acid that has been removed from its natural environment.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

As used herein, the term "germline competent chicken cell" refers to a cell that is able to contribute to the germ line of a chicken and transmit target loci to progeny. Such a cell may be present in vitro (i.e., a cultured cell) or in vivo (i.e., in a living chicken).

The terms "gene" and "locus" are used interchangeably herein. Neither term implies that a gene is actively transcribed or intact. Both terms encompass genes that have been inactivated.

The term "inactivated" is intended to indicate a gene that is not expressed in the sense that the protein encoded by the gene is not expressed. Genes can be inactivated by removing a portion of a coding sequence and/or regulator sequence of a gene. A gene that is disrupted, e.g., "knockout", is a type of inactivated gene. A locus that once contained an expressed endogenous sequence that has since been replaced by a human immunoglobulin sequence that is also expressed contains an inactivated endogenous gene. As such, a locus that contains an expressed human immunoglobulin sequence can have an inactivated endogenous immunoglobulin gene if the endogenous immunoglobulin gene was replaced by the human immunoglobulin sequence. In many case this may be done by knocking out the endogenous sequence (e.g., by deletion of at least part of the sequence) and then inserting the human immunoglobulin sequence at a position that was once occupied by the endogenous sequence.

The term "corresponding", in the context of two nucleotide sequences, is intended to indicate that the sequences are share significant sequence identity and are positioned across from one another if two sequences are aligned. For example, the JH region of one heavy chain immunoglobulin locus corresponds to the JH region of another heavy chain immunoglobulin (e.g., one from another animal) if the sequences align with one another and positioned in a similar way relative to other sequence elements.

The term "in vitro" refers to a cell that in culture, i.e., outside of an organism.

The term "in vivo" refers to a cell that is in a living organism.

As used herein, the term "gonocyte" refers to a germ cell in a differentiated gonad that is responsible for gametogenesis (i.e., spermatogenesis in males and oogenesis in females). Gonocytes include gametogonia (spermatogonia and oogonia), oocytes, ootids, and ova. The term "gonocyte" is intended to explicitly exclude primordial germ cells that are migrating and have not yet taken up residence in an undifferentiated gonad.

The term "primordial germ cell" refers to cells that, in an animal, are migrating and have not yet taken up residence in an undifferentiated gonad. Such cells may be cultured in vitro and implanted into an animal. After implantation, those cells can migrate and take up residence in the gonad.

As used herein, a "chimeric" chicken is a chicken containing a significant number of genetically distinct cells from at least two sources. A chimeric animal may be made by implanting cells from one animal into an embryo of another animal, or by implanting cultured cells (that, e.g., have a modified genome) into an embryo. The implanted cells may be harvested from a culture prior to incorporation into the host embryo. The embryo develops into an animal, and the resultant animal may contain cells from the host as well as the implanted cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

Further definitions may be elsewhere in this disclosure.

DETAILED DESCRIPTION

Before the present subject invention is described further, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Germline Competent Cells

A germline competent chicken cell comprising an endogenous heavy chain immunoglobulin locus that has been inactivated is also provided. In particular embodiments, this cell may contain a knockout of the endogenous heavy chain immunoglobulin locus in which at least the JH region of the locus has been replaced by a selectable marker. Germline competent chicken cells that contain a genome in which both the endogenous heavy and light chain immunoglobulin loci have been inactivated are also provided.

A germline competent chicken cell comprising an endogenous light chain immunoglobulin locus in which the endogenous V-J-C region has been inactivated is also provided. In particular embodiments, this cell may contain a knockout of the endogenous light chain immunoglobulin locus in which the endogenous V-J-C region has been replaced by a selectable marker. Removal of the endogenous V region from the endogenous light chain immunoglobulin locus provides a locus that is not expressed in that the locus is not transcribed and no transcript is detected.

The germline competent chicken cell may be present in vitro (i.e., may be a cultured cell) or in vivo (i.e., may be in a living chicken, e.g., a chicken embryo). The cell may be, for example, a gonocyte or a primordial germ cell, both of which cell types are present in chicken embryos and can be cultured and manipulated in vitro (see, e.g., U.S. patent application Ser. No. 12/986,868, filed on Jan. 7, 2011 and references cited therein). Both gonocytes and primordial germ cells can contribute to the germ line when implanted into a chicken embryo.

Methods for culturing primordial germ cells as well as for introducing nucleic acid into the same are well established. Examples of such methods are described in Allioli et al (Dev Biol. 1994 165:30-7), Chang et al (Cell Biol. Int. 1995 19:143-9), Chang et al, (Cell Biol. Int. 1997 21:495-9), Han et al (Mol. Reprod. Dev. 2005 72:521-9), van de Lavoir et al, (Nature 2006 441: 766-9) Shiue et al (Reprod. Domest. Anim. 2009 44:55-61) and Park et al, (Biol. Reprod. 2003 68:1657-62). Cultured chicken primordial germ cells are also discussed in the following reviews: Kerr et al (Methods Enzymol. 2006 419:400-26), Petitte et al (Mech. Dev. 2004 121: 1159-68) and Petitte et al (Poult Sci. 1997 76:1084-92). Methods for culturing chicken gonocytes as well as for introducing nucleic acid into the same are described in U.S. patent application Ser. No. 12/986,868, filed on Jan. 7, 2011 and in Leighton et al (Mol. Reprod. Dev. 2008 75: 1163-75).

Targeting Vectors

Vectors for inactivating the light and/or heavy chain immunoglobulin locus of a chicken genome are also provided.

In certain embodiments, the vector is for inactivating the heavy chain immunoglobulin locus of a chicken genome. In these embodiments, the vector may comprise, in order from 5' to 3': a) a sufficient length of sequence 5' of the JH region of the heavy chain immunoglobulin locus to effect homologous recombination; b) a selectable marker cassette; and c) a sufficient length of sequence 3' of the JH region of the heavy chain immunoglobulin locus to effect homologous recombination. In certain embodiments, the vector may comprise, in order from 5' to 3': a) at least 400 nt (e.g., at least 500 nt, at least 1 kb, at least 2 kb or at least 5 kb) of sequence 5' of the JH region of the heavy chain immunoglobulin locus; b) a selectable marker cassette; and c) at least 400 nt (e.g., at least 500 nt, at least 1 kb, at least 2 kb or at least 5 kb) of sequence 3' of the JH region of the heavy chain immunoglobulin locus. This vector may be designed to leave the endogenous array of V pseudogenes, the VH region, the D cluster, the J-Cmu intron, the constant regions, and the 3' untranslated region of the endogenous heavy chain locus intact, as shown in the figures. In some cases, the vector does not contain the JH region. In particular cases, vector may contain a nucleotide sequence that is at least 95% identical to nucleotides 1760 to 1957 of SEQ ID NO:15. Likewise, in some embodiments, the vector may contain a nucleotide sequence that is at least 95% identical to nucleotides 2865-4932 of SEQ ID NO:15.

In certain embodiments, the vector is for inactivating the light chain immunoglobulin locus of a chicken genome. In these embodiments, the vector may comprise, in order from 5' to 3': a) a sufficient length of sequence 5' of the V region of the light chain immunoglobulin locus to effect homologous recombination; b) a selectable marker cassette; and c) a sufficient length of sequence 3' of the C region of the light chain immunoglobulin locus to effect homologous recombination. In particular embodiments, the vector may comprise, in order from 5' to 3': a) at least 400 nt (e.g., at least 500 nt, at least 1 kb, at least 2 kb or at least 5 kb) of sequence 5' of the V region of the light chain immunoglobulin locus; b) a selectable marker cassette; and c) at least 400 nt (e.g., at least 500 nt, at least 1 kb, at least 2 kb or at least 5 kb) 3' of the C region of said light chain immunoglobulin locus. This vector may be designed to leave the endogenous array of V pseudogenes intact, and the 3' untranslated region of the endogenous light chain locus intact, as shown in FIG. 1.

In a particular embodiment, the vectors may contain: a) at least one selectable marker flanked by lox sites, b) an att site (e.g., an attP site) that is not between the lox sites and c) an optional selectable marker between the att site and the closest lox site. After the targeting vector is inserted into the locus, the part of the vector that is between the lox sites can be deleted using cre recombinase, and clones containing the deletion can be selected by the optional selectable marker. After the part of the vector that is between the lox sites has been deleted, a human immunoglobulin sequence (containing, e.g., a human V-J or J region) can be inserted at the attP site of the construct using a suitable recombinase (e.g., a suitable bacteriophage recombinase).

As illustrated in the figures, the selectable marker cassette may contain one or more selectable markers, reporter proteins and sites for a recombinase (e.g., lox sites) that can be employed to select and identify cells as well delete sequences, as desired. The construction of targeting vectors for gene disruption is generally well known (see, e.g., Arakawa et al (Subcell Biochem. 2006 40:1-9), Winding et al (J Immunol Methods 2001 249: 1-16) and Müller (Mech Dev. 1999 82: 3-21). See also, Ausubel, et al, *Short Protocols in Molecular Biology*, 9rd ed., Wiley & Sons, 2007; Sambrook, et al., *Molecular Cloning: A Laboratory Manual*, Second Edition, (2001) Cold Spring Harbor, N.Y.).

Chimeric and Transgenic Chicken

Also provided is a chimeric chicken comprising an above-described cell in the germline of the chicken. Gonocytes may be implanted into a recipient embryo by, e.g., injection into the subgerminal cavity, injection into the germinal crescent, or by injection into the bloodstream, for example. The term "implanting" is intended to encompass direct (e.g., injection directly into a region) and indirect (e.g., systemic administration) methods by which cells are placed in a region of an embryo.

Methods for implanting germline competent cells into a recipient chicken embryo to produce a germline chimera are described in many of the references cited above and in, for example, Mozdziak et al, (Poultry Science 2006 85: 1764-1768), Naito et al, (Reproduction 2007 134: 577-584), Petitte et al (Development 1990 108:185-189) and Mozdziak et al (Dev. Dyn. 2003 226:439-445). In this method, the embryos may be cultured in a surrogate chicken eggshell, followed by a surrogate turkey eggshell, until hatching, following procedures modified from Borwornpinyo et al (*Culture of chicken embryos in surrogate eggshells* Poult. Sci. 2005 84:1477-1482). In an alternative method, chicken eggs may be pre-treated with an injection of a busulfan emulsion into the yolk of embryos after 24 h of incubation, according to the methods by Song et al (Mol. Reprod. Dev. 2005 70:438-444). After busulfan injection, the eggs may be returned to the incubators until they reach stage 17 (Hamburger, V., and H. L. Hamilton. 1951. A series of normal stages in the development of the chick embryo. J. Morphol. 88:49-67) when they are injected through the dorsal aorta with 600 to 3,500 cells. After injection, the eggshells can be sealed, and the eggs returned to the incubator and maintained until hatching. Naito et al, supra, describes a method by which gonocytes are injected into the bloodstream of a recipient animal. In a further example, embryos at 3 d of incubation may be injected with 1,000 to 2,000 gonocytes into the germinal crescent. The injected embryos may be cultured in a surrogate turkey eggshell until hatching, following the procedures of Borwornpinyo et al. (*Culture of chicken embryos in surrogate eggshells*. Poult. Sci. 2005 84:1477-1482). See also van de Lavoir et al, (Nature. 2006 441: 766-9).

The resultant embryo containing implanted cells may be incubated to produce a chimeric bird containing germ-line cells that are derived from the implanted cells. The progeny of such a chimeric chicken may be fully transgenic, although heterozygous for the genome modification. The progeny may be mated with other chickens to produce further progeny that may be heterozygous or homozygous for the genome modification. Alternative methods for making transgenic chickens are known.

A transgenic chicken comprising an inactivated heavy and/or light chain immunoglobulin locus is therefore provided. In certain embodiments, both the heavy and light chain loci of the transgenic chicken may be inactivated. The chicken may be homozygous or heterozygous for the inactivated heavy chain locus and/or the inactivated light chain locus.

In certain cases, no antibody expression is detectable using, e.g., ELISA, in a transgenic chicken that is homozygous for the inactivated heavy chain locus and/orhomozygous for the inactivated light chain locus.

Isolated Polynucleotides and Host Cells Containing the Same

Also provided herein is an isolated polynucleotide comprising the JH region of a chicken heavy chain immunoglobulin locus, as well as at least 500 bases of flanking sequence on both sides of the JH region in the chicken heavy chain immunoglobulin locus. In particular embodiments, the isolated polynucleotide may comprise: a) the JH region of the chicken heavy chain immunoglobulin locus; b) at least 500 bp (e.g., at least 600 bp, at least 700 bp, at least 800 bp, at least 900 bp, at least 1 kb, at least 1.5 kb, or at least 2 kb or more of the sequence that flanks the JH region on the 5' side of the JH region; and at least 500 bp (e.g., at least 600 bp, at least 700 bp, at least 800 bp, at least 900 bp, at least 1 kb, at least 1.5 kb, or at least 2 kb or more of the sequence that flanks the JH region on the 3' side of the JH region. In certain embodiments, the sequence of the JH region and/or the flanking sequence may be at least 85% (e.g., at least 90%, at least 95%, at least 97%, at least 98%, or at least 99% identical) to a sequence of SEQ ID NO:15, thereby accommodating sequencing errors, SNPs and other genotype-specific differences between sequences, where the JH region corresponds to nucleotides of SEQ ID NO: 15 the 2324-2380, and the flanking sequence may be defined by nucleotides 1760 to 1957 of SEQ ID NO:15 and/or nucleotides 2865-4932 of SEQ ID NO:15. The total length of the isolated polynucleotide may be up to, e.g., 10 kb or 20 kb or more, although constructs having a length that is greater than 20 kb are envisioned. The isolated polynucleotide may be contained in a non-chicken host cell, e.g., in a vector or integrated into the genome. The host cell may be of any species, including bacteria, a non-chicken bird, or yeast, etc.

Utility

The above-described chicken, particularly a transgenic chicken that has both an inactivated heavy chain gene and an inactivated light chain gene, may be employed to make fully human antibodies that have therapeutic potential. In particular embodiments, the genome of the transgenic chicken may be further modified to contain human immunoglobulin sequences (e.g., human germline sequences) so that human antibodies can be produced by the chicken. The inactivation of the endogenous heavy and light chain loci allows the expression of human immunoglobulin sequences that can be inserted into the loci without any interference from transcriptional activity and/or RNA transcribed from the endogenous loci. A deletion of only the J-C of the light chain immunoglobulin locus does not abolish transcription of the light chain immunoglobulin locus and, as such, the locus is not inactivated. The expression of human immunoglobulin sequences that are inserted downstream of such a deletion may be inhibited by this activity and/or the RNA produced thereby. In one embodiment, the chicken genome may be modified to provide for the production of antibodies that contain a synthetic V region (see e.g., U.S. 20110055938, which is incorporated by reference in its entirety, including all figures and strategies for making such antibodies, for disclosure of such methods). Methods for isolating sequences for antibodies can be produced by such a system are well known (see, e.g., U.S. 2010/0092955, which is incorporated by reference in its entirety, including all figures and strategies for making such identifying such, for disclosure of such methods,).

EXAMPLES

The following examples are provided in order to demonstrate and further illustrate certain embodiments and aspects of the present invention and are not to be construed as limiting the scope thereof.

Example 1

IgL-VJC Knockouts

In this method, the functional V region and promoter are removed in addition to the J and C regions. By removing the V region and promoter, there is no possibility of expression of the functional V in the knockout allele. Expression of the V region by itself (without J and C) would not be functional but could complicate further uses of the knockout chicken. For example, if transgenes for the expression of human antibodies are introduced into the IgL-JC knockout chicken, the remaining V region could potentially interfere with expression of the human antibodies.

A targeting vector was prepared with 1023 bp 5' homology to the promoter region of the functional chicken VL gene and 7196 bp of 3' homology to the region downstream of the C region. The vector deletes a total of 5840 bp including the V, J, C regions and 1289 bp of the V region promoter. The knockout inserts a selectable marker cassette including an EGFP gene, a puromycin resistance gene, and a promoterless neomycin resistance gene with an attP site. The selectable markers are flanked by loxP sites for later excision with Cre recombinase. The homology regions were cloned by genomic PCR from the cell line WL43 used for gene targeting experiments.

Figure 2:
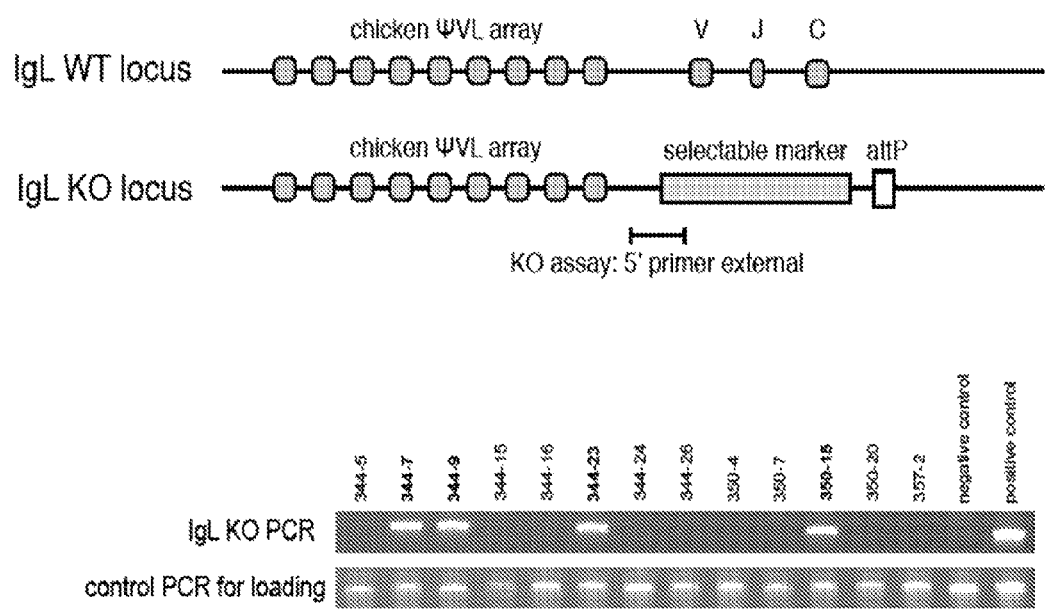
FIG. 2 illustrates the resultant IgL-VJC knockout, and is a gel showing the targeting of the light chain locus in primordial germ cells. A total of four knockout clones were found in this experiment.

The IgL knockout vector was linearized and electroporated into two PGC cell lines, WL43 and Nu69. Clones were selected with puromycin and analyzed by PCR for the knockout (FIG. 2).

TABLE 1

Frequency of targeting the light chain in PGCs. The number of targeted clones out of the total number of clones screened is shown.

| Cell line | Frequency |
|---|---|
| WL43 | 18/58 (31%) |
| Nu69 | 9/60 (15%) |

Figure 3:
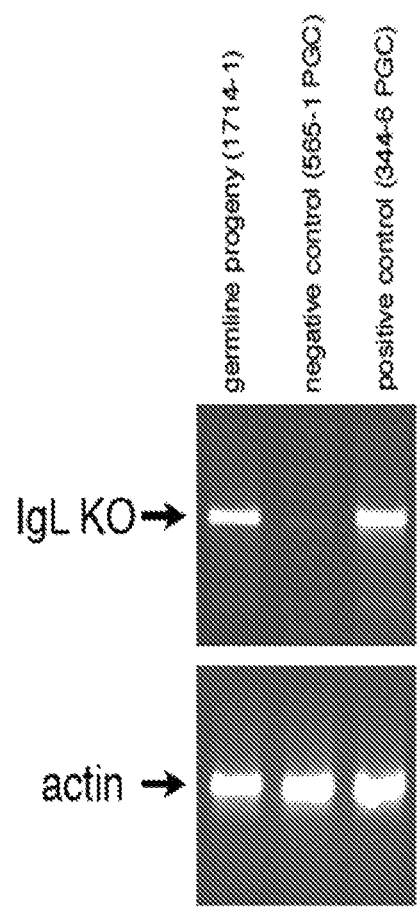
FIG. 3 shows germline transmission of IgL KO. The PCR assay shown in FIG. 2 was used to detect the IgL KO in germline progeny from chimera 1714 (cell line 438-3).

Several IgL KO clones were injected into embryos to produce germline chimeras to pass the knockout to the next generation. As shown in FIG. 3, germline transmission was obtained. The germline progeny in this case was euthanized in order to establish a newly derived gonadal cell line carrying the knockout. Germline transmission from two cell lines was obtained (438-3 and 624-3).

The primers used for the knockout assay are as follows: forward primer in chIgL 5' flanking region: 5'-actgtgctgcag-gtggctatg-3' (SEQ ID NO:1); reverse primer in selectable marker cassette: 5'-atacgatgttccagattacgctt-3' (SEQ ID NO:2); control primers for loading (in chIgL locus): 5'-act-gtgctgcaggtggctatg-3' (SEQ ID NO:3); and reverse primer: 5'-tcagcagcagcagtgcggac-3' (SEQ ID NO:4). The IgL KO2B sequence is shown in SEQ ID NO:5.

Example 2

IgH Knockouts

To create a null mutation in the chicken heavy chain locus, the single JH segment was deleted, which is a necessary domain in all immunoglobulins produced by the endogenous immune system.

Figure 4:
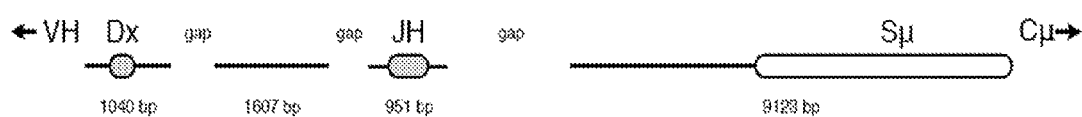
FIG. 4. illustrates sequencing of chicken genomic region surrounding single JH segment. Top line, compilation of published and genome database sequences with position of gaps indicated. The sizes of each contig are shown below the line. Bottom diagram shows Crystal's 9736 bp contig, with 2.3 kb upstream and 7.4 kb downstream of the 57 bp JH segment, extending into the Sµ region. No D sequence was identified.
Figure 4:
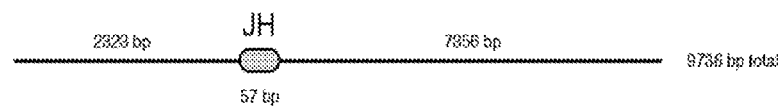
Figure 5:
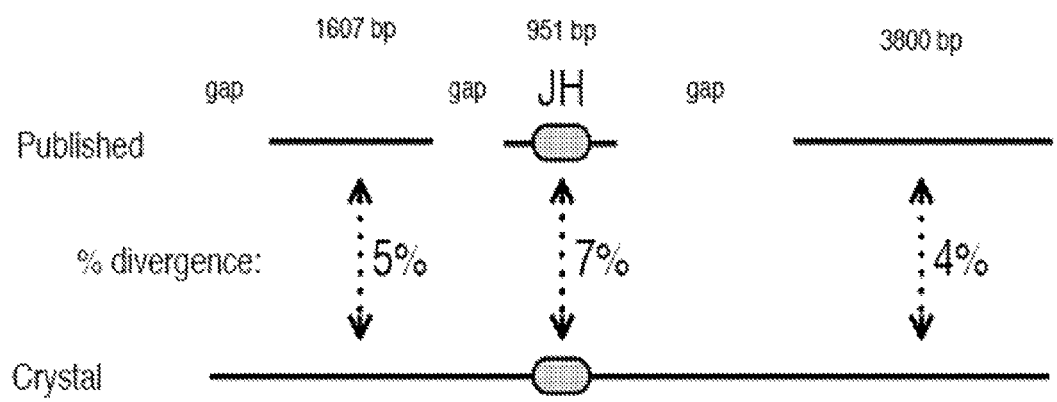
FIG. 5 schematically illustrates the sequence divergence between published genome sequences and the obtained IgH sequence.

To design a targeting vector that deletes the JH segment in chicken PGCs, it was first necessary to identify genomic flanking sequences to use as 5' and 3' homology regions. The chicken genome databases were queried, using the published JH and D sequences (Reynaud et al Cell. 1989 59:171-83) and published sequence near the Sμ switch region. Several contigs could then be assembled in silico, although gaps remained between the D, JH and switch region contigs (FIG. 4). These gaps needed to be bridged in order to build a targeting vector for the JH segment. PCR was used to amplify products across the region, spanning the gaps. PCR was performed using template genomic DNA from the PGC cell line used for targeting (Nu69, aka WL43). Alignment of these PCR product sequences produced a single long contig spanning over 9.7 kb around the JH segment, from 2.3 kb upstream to 7.4 kb downstream of the JH (FIG. 5). Comparison of these sequences to the available database sequences showed a high degree of sequence divergence (FIG. 5). The new sequence indicates that the gaps in the published sequence are predicted to be about 200 bp on the 5' side of JH and about 2 kb on the 3' side.

Figure 6:
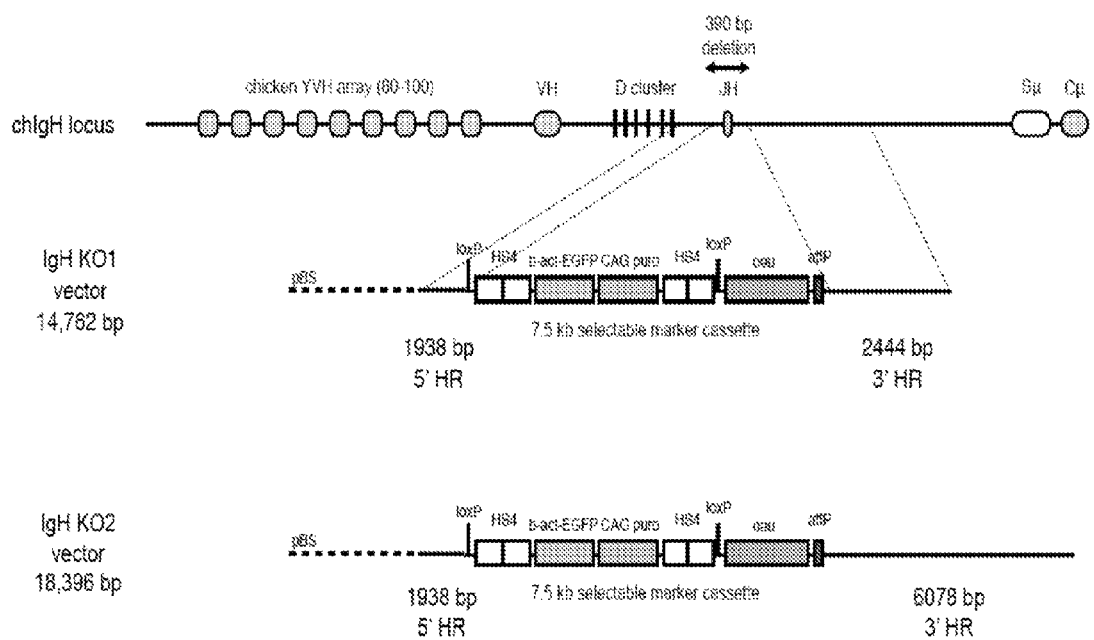
FIG. 6 schematically illustrates vectors IgH KO1 and IgH KO2 that are designed to delete the JH segment.

Using the sequences amplified from the PGC cells, two targeting vectors were prepared, identical except for varying lengths of 3' homology regions. The 5' HR in both vectors is 1938 bp, and the 3' HR is either 2444 bp (IgH KO1; FIG. 6) or 6078 bp (IgH KO2; FIG. 6). A selectable marker cassette containing the chicken β-actin promoter driving the EGFP gene, a puromycin selectable marker driven by the CAG promoter and a promoterless neo selectable marker with attP site was included. HS4 insulators from the chicken β-globin gene flank the EGFP and puro genes, and loxP sites are included for Cre-mediated excision of EGFP and puro. These vectors are designed to delete 390 bp from the chicken genome including the single JH region.

Figure 7:
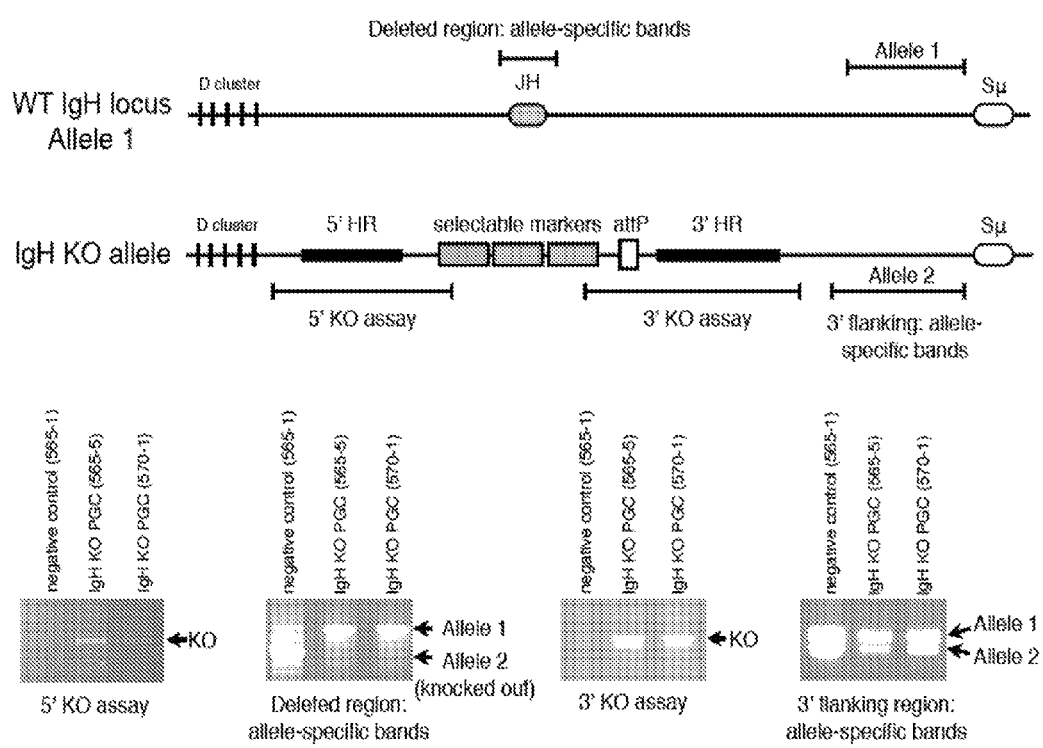
FIG. 7 shows results of a PCR analysis of targeting the JH segment in PGCs using IgH KO1. Two knockout clones and one wild type (WT) control clone are shown. Locations of the PCR products are indicated in the diagrams.

The IgH KO1 vector was linearized with NotI and electroporated into PGC cell line WL43, the source of the homology region sequences. From 8 transfections, 29 clones were isolated. Several sets of primers were used to screen the clones. Primers were used to detect the targeted insertion on both the 5' and 3' sides of insertion, where one primer hybridizes to the flanking genomic region (not present on the targeting vector) and the other primer hybridizes to the selectable marker cassette (FIG. 7). The loss of the JH region was confirmed using primers which detect different sized products from the two alleles in WL43 cells. In WL43, the two alleles show many polymorphisms, including single nucleotide polymorphisms and insertions/deletions of moderate length which can result in different sized PCR products. In the knockout cells, one of the two PCR bands, corresponding to one of the alleles, was consistently absent, indicating the knockout of that allele. The other allele consistently amplified, as expected for a heterozygous cell line. As a control, PCR was performed using primers from a nearby region of the heavy chain locus which also produce different sized products from the two alleles, to confirm that a general loss of the region (such as loss of a chromosome) had not occurred. Both alleles amplified from this flanking region, indicating presence of both alleles in regions of the heavy chain that should not be affected by the knockout of the JH region.

The 5' KO assay product was sequenced and showed the expected sequence for the knockout. FIG. 7 shows the analysis of two clones using all four PCR assays. For the majority of clones, only the 5' assay and the deleted region assay were performed.

Figure 8:
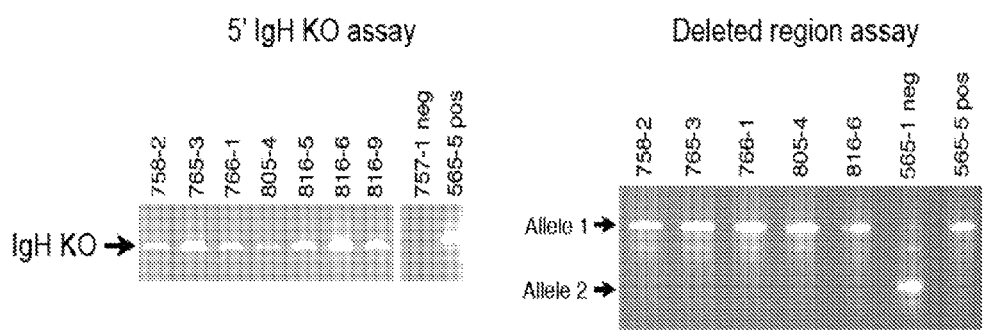
FIG. 8 shows the results of PCR analysis of targeting the JH segment using the IgH KO2 vector. Analysis of a subset of the clones is shown. The 5' IgH KO assay and Deleted region assays both indicated the correct targeting event.

The IgH KO2 vector was linearized with NotI and electroporated into PGC cell line WL43 (aka Nu69). From 41 transfections, a total of 81 stable transfected clones were obtained. Of these clones, 59 were expanded for analysis of gene targeting, and targeting was observed in 15 clones, for a frequency of approximately 25%. The clones were analyzed by PCR for the 5' assay and deleted region assay (FIG. 8). No 3' KO assay was performed owing to the much longer 3' homology region in this vector.

PGC clones carrying the IgH KO were injected into embryos at day 3 of incubation in order to produce chimeric chickens with the knockout PGCs in the germline. These embryos contained a mixture of PGCs of their own plus the injected cells carrying the chicken heavy chain knockout. The embryos were incubated, the chicks were hatched and animals were grown to sexual maturity. These birds are referred to as the G0 generation. To pass the genetic modification on to the the next generation, the germline chimeras were bred to normal, wild type chickens and progeny were tested for those that inherit the modification. The heavy chain knockout allele contains the gene encoding green fluorescent protein (GFP) that causes the birds to glow green under illumination with a handheld UV lamp, allowing us to screen quickly for germline transmission. These birds are called heterozygotes of the G1 generation, for they are the first generation to carry the genetic modification in all cells of the body, not just the germline. These G1 birds are then bred to wild type chickens to propagate the line, or heterozygotes are mated to each other to produce homozygous animals.

Figure 9:
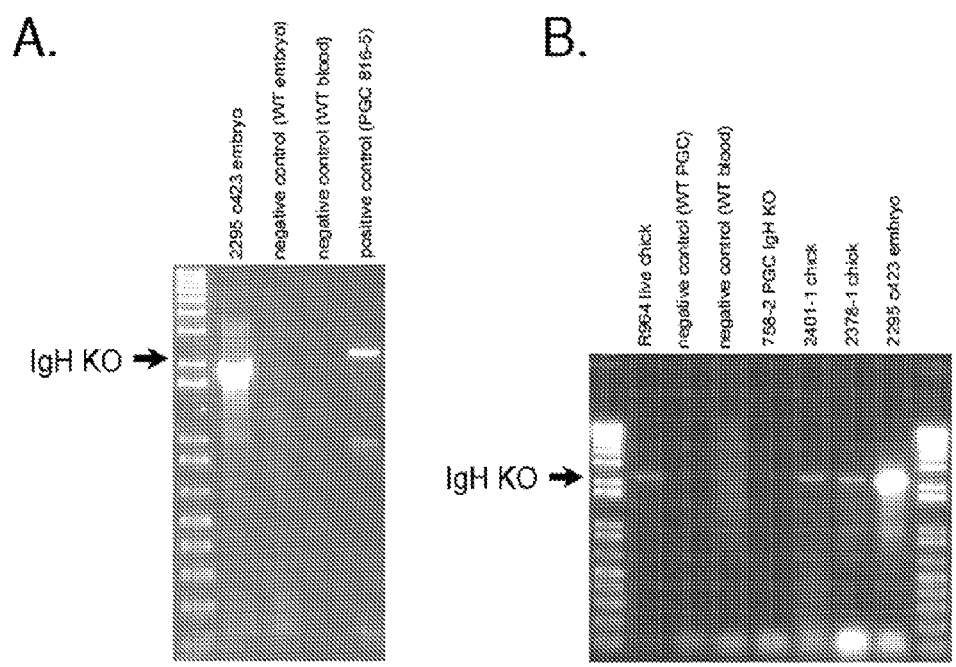
FIG. 9 panel A shows the results of a PCR analysis using the 5' KO assay for the IgH KO was performed on a GFP-positive embryo obtained from breeding chimera 2295. A very strong amplification was obtained from the embryo relative to the positive control (an IgH KO PGC line), probably owing to increased amount of genomic DNA in the sample. Wild type genomic DNA served as negative controls. Panel B. A live chick, R964, is shown to carry the IgH KO. PCR for the IgH KO was performed on comb biopsy DNA. Germline transmission in two other chicks was also observed (2401-1 and 2378-1) although these chicks did not survive.

For the heavy chain knockout, several chimeric G0 birds have produced germline progeny in which the knockout was transmitted to the next generation. Presence of the knockout in live birds was confirmed by PCR using the 5' KO assay (FIG. 9). The cell lines 758-2 and 805-4 (FIG. 8) have produced germline progeny.

The primers used in the PCR assays are as follows:

```
5' KO assay:
                                              (SEQ ID NO: 6)
    chDJ-F1          CAGTGTCCAAATTCCTTAAATTTCC;

(SEQ ID NO: 7)
    HA-R             ATACGATGTTCCAGATTACGCTT
```

```
Deleted region
                                              (SEQ ID NO: 8)
    chDJ-F7          TGAACCCATAAAGTGAAATCCTC (SEQ ID NO: 9)
    chJH-R3          TTCGGTCCCGTGGCCCCAT 3' KO assay
                                              (SEQ ID NO: 10)
    neo-R4           GGAACACGGCGGCATCAGAGCA (SEQ ID NO: 11)
    chJC-R6a2        CCGGAAAGCAAAATTTGGGGGCAA 3' flanking region
                                              (SEQ ID NO: 12)
    chJC-F10         GGGGGTTCGGTGCAGTTTTTC (SEQ ID NO: 13)
    chJC-R14         ATATTGGCCCCATTTCCCCTCAG
```

The sequence of the IgH KO and KO2 vectors are set forth as SEQ ID NOS:14 and 16, respectively. The sequence of 9736 bp of the chicken IgH locus surrounding the JH segment is set forth as SEQ ID NO:15. The JH segment is represented by nucleotides 2324-2380 of this sequence. The newly identified sequence 5' of the JH segment is defined by nucleotides 1760 to 1957 of SEQ ID NO:15. The newly identified sequence 3' of the JH segment is defined by nucleotides 2865 to 4932 of SEQ ID NO:15.

What is claimed is:

1. A system comprising:
   (a) a vector for inactivating the endogenous heavy chain immunoglobulin locus of a chicken genome, comprising, in order from 5' to 3':
      at least 400 bp 5' of the JH region of said heavy chain immunoglobulin locus;
      a selectable marker cassette; and
      at least 400 bp 3' of the JH region of said heavy chain immunoglobulin locus,
      wherein said vector does not contain said JH region; and
   (b) a chicken primordial germ cell;
      wherein the at least 400 bp 5' of the JH region of (a) and the at least 400 bp 3' of the JH region of (a) are amplified from and/or have the same sequence as heavy chain immunoglobulin locus of the chicken primordial germ cell of (b).

2. The system of claim 1, wherein said vector does not does not contain the VH or C regions of said endogenous heavy chain immunoglobulin locus.

3. The system of claim 1, wherein said at least 400 bp 5' of the JH region comprises a nucleotide sequence that is at least 95% identical to nucleotides 1760 to 1957 of SEQ ID NO:15.

4. The system of claim 1, wherein said at least 400 bp 3' of the JH region comprises a nucleotide sequence that is at least 95% identical to nucleotides 2865-4932 of SEQ ID NO:15.

* * * * *